United States Patent [19]

Nau et al.

[11] Patent Number: 5,786,380
[45] Date of Patent: Jul. 28, 1998

[54] VPA-ANALOGOUS ANTIEPILEPTICS

[76] Inventors: Heinz Nau, Hegauer Weg 43, 14163 Berlin; Ursula Bojic, Grunewaldstr. 27, 12165 Berlin; Ralf-Siegbert Hauck, Steglitzer Damm 72, 12169 Berlin, all of Germany; Mohamed Mohey Eldin Elmazar, 6 Ahmed El-Shediak Str. Ard El-Golf, Heliopolis, Cairo, Egypt

[21] Appl. No.: 344,810

[22] Filed: Nov. 23, 1994

[30] Foreign Application Priority Data

Sep. 12, 1992 [DE] Germany .................. 42 31 085.7

[51] Int. Cl.$^6$ .................................................. A61K 31/19
[52] U.S. Cl. ................ 514/557; 562/506; 562/598; 562/606; 554/1; 554/223; 514/558; 514/560; 514/578; 514/572
[58] Field of Search ................... 562/506, 598, 562/606; 554/223, 1; 514/557, 558, 560, 572, 578

[56] References Cited

U.S. PATENT DOCUMENTS 3,325,361  6/1967  Meunier .

OTHER PUBLICATIONS

Haj–Yehia, Abdulla and Bialer, Meir (1990) *J. Pharm. Sci.* 79:8, 719–724 (Exhibit C).
Hauck and Nau (1989) *Toxicol. Lett.* 49:41–48 (Exhibit D).
Hauck and Nau (1991) *Naturwissenschaften* 78:272–274 (Exhibit E).
Hauck, et al. (1992) *Toxicol. Lett.* 60:145–153 (Exhibit F).
Nau, et al., (1981) *J. Pharmacol. Exp. Ther.* 219:768–777 (Exhibit I).
Nau, et al., (1991) *Pharmacol. and Toxicol.* 69:310–321 (Exhibit J).
Okada, Katsuhide, et al., (1980) *Agric. Biol. Chem.*, 44(11), 2595–2599 (Exhibit K).
Wilson, Stephen R., (1993) *Proc. Workshop Vitam. D., 6th(Vitam. D)*, 749–754, New York University, NY, NY 10003 (Exhibit L).
Kurth, Mark J. and Brown, Edward G., (1987) *J. Am. Chem. Soc.*, 109(22), 6844–5 (Exhibit G).
Kurth, Mark J., et al., (1988) *Tetrahedron Lett.*, 29(13), 1517–1520 (Exhibit H).
Wilson, Stephen R., (1993) *Proc. Workshop Vitam. D., 6th(Vitam. D)*, 749–754, New York University, NY, NY 10003 (Exhibit L).

*Primary Examiner*—Michael L. Shippen
*Attorney, Agent, or Firm*—Morgan & Finnegan, L.L.P.

[57] ABSTRACT

The invention provides compounds which are effective antiepileptics and at the same time display only a slight sedative and teratogenic effect and have the formula

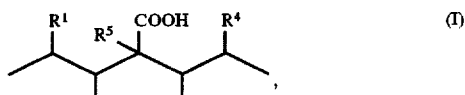

(I)

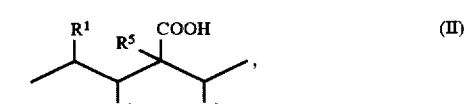

(II)

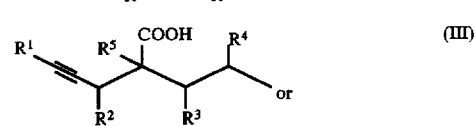

(III)

or

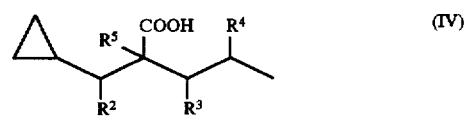

(IV)

where the compounds of the formulae (I) and (II) can also be mono- or polyunsaturated, in which $R^1$, $R^2$, $R^3$ and $R^4$ are each, independently of one another, hydrogen or a $C_1$–$C_6$-alkyl group, $R^5$ is hydrogen or a $C_1$–$C_2$-alkyl group, and at least one of the radicals $R^1$ to $R^4$ in the compounds of the formulae (I) and (II) is different from hydrogen, where the compounds of the formula (I), in the case where a center of asymmetry is present on the carbon atom in position 2, and the compounds of the formulae (II), (III) and (IV) are in the form of their racemate, their pure enantiomers or a mixture of their enantiomers which differs from the racemate, and pharmaceutically compatible salts thereof.

6 Claims, 9 Drawing Sheets

VPA-ANALOGOUS ANTIEPILEPTICS

This is a continuation-in-part application of International Application PCT/DE93/00861.

FIELD OF THE INVENTION

The invention relates to compounds which are analogs of valproic acid, to the use thereof as antiepileptic and to the preparation thereof.

BACKGROUND OF THE INVENTION

Epilepsy is a chronic disease from which about 0.5% to 2% of the population suffers. Valproic acid (2-n-propylpentanoic acid), for example, has been proposed as antiepileptic. Besides the antiepileptic (anticonvulsant) action, valproic acid may lead to teratogenic and sedative (neurotoxic) effects. Almost 1% of all pregnant women suffer from epilepsy. The risk of malformation for children of mothers with epilepsy is 1½ to 3 times higher than for healthy mothers. The causes of the increased incidence of malformations are probably multifactorial, it being possible for not only the antiepileptics but also genetic factors as well as the type and severity of the epilepsy to play a part. It has also emerged with valproic acid that more children with malformations were born.

There has thus been no lack of attempts to find other compounds which have equally potent or more potent antiepileptic effects and which have a lower teratogenicity than valproic acid and only a slight sedative action. Thus, for example, 2-n-propyl-2-pentenoic acid, 2-n-propyl-3-pentenoic acid, 2-n-propyl-4-pentenoic acid and 2-n-propyl-4-pentynoic acid have been proposed as antiepileptics. However, some of these compounds have considerable teratogenic effects, and the antiepileptic effect is in fact less than that of valproic acid.

The invention is therefore based on the object of providing compounds which are effective antiepileptics and moreover show only a slight sedative and teratogenic effect.

SUMMARY OF THE INVENTION

This object is achieved by compounds having the formula

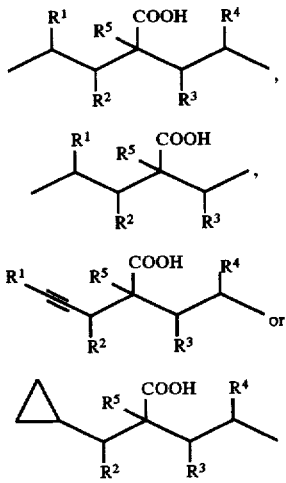

where the compounds of the formula (I) and (II) can also be mono- or polyunsaturated, in which $R^1$, $R^2$, $R^3$ and $R^4$ are, independently of one another, hydrogen or a $C_1$–$C_6$-alkyl group, $R^5$ is hydrogen or a $C_1$–$C_2$-alkyl group, and at least one the radicals $R^1$ to $R^4$ in the compounds of the formulae (I) and (II) is different from hydrogen, where the compounds of the formula (I) are, when a center of asymmetry is present on the carbon atom in position 2, in the form of their racemate, their pure enantiomers or a mixture of their enantiomers which differs from the racemate, and the compounds of the formulae (II), (III) and (IV) are in the form of their pure enantiomers or a mixture of their enantiomers which differs from the racemate, where the compounds of the formula (III) are, when they are alkylated in at least one position different from position 5, and the compounds of the formula (IV) are, when they are alkylated at least once, also in the form of their racemate, as well as pharmaceutically compatible salts thereof.

This invention also relates to pharmaceutical compositions which are effective as antiepileptics comprising the compounds of the invention and a pharmaceutically acceptable carrier. In addition, this invention relates to methods of treating individuals with epilepsy by administering therapeutically effective amounts of the disclosed compounds.

The antiepileptic according to the invention comprises a compound of the formula

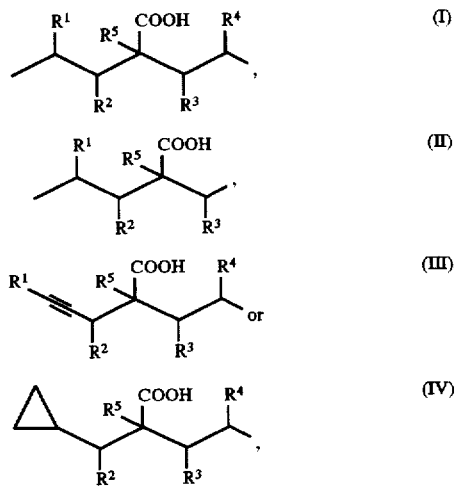

where the compounds of the formulae (I) and (II) can also be mono- or polyunsaturated, in which $R^1$, $R^2$, $R^3$ and $R^4$ are each, independently of one another, hydrogen or a $C_1$–$C_6$-alkyl group, $R^5$ is hydrogen or a $C_1$–$C_2$-alkyl group, and at least one of the radicals $R^1$ to $R^4$ in the compounds of the formulae (I) and (II) is different from hydrogen, where the compound of the formula (I) is, in the case where a center of asymmetry is present on the carbon atom in position 2, and the compounds of the formulae (II), (III) and (IV) are in the form of their racemate, their pure enantiomers of a mixture of their enantiomers which differs from the racemate, or pharmaceutically compatible salts thereof.

DETAILED DESCRIPTION

Figure 1:
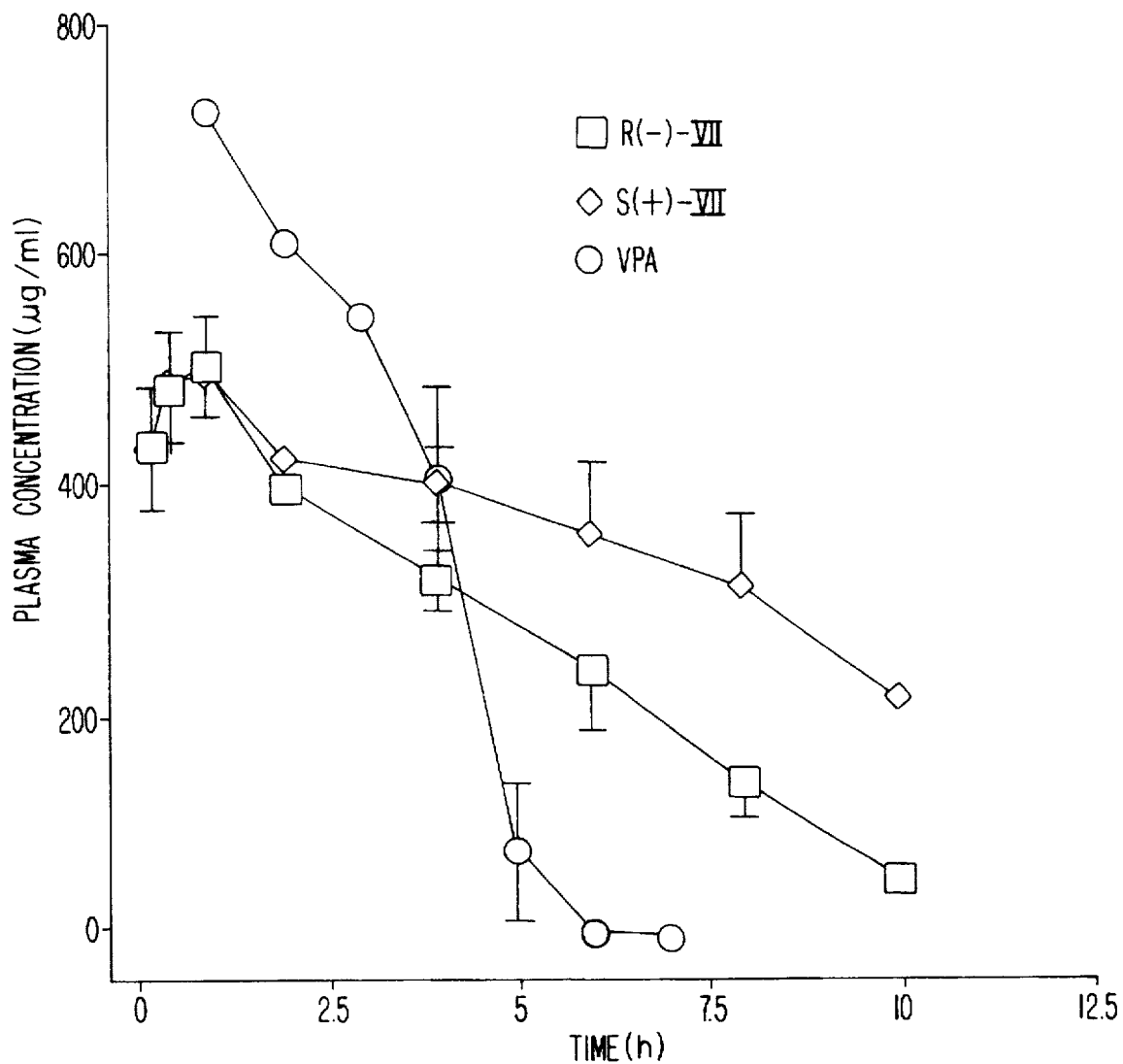
FIG. 1 Plasma kinetics of valproate (3.0 mmol/kg) and the R- and S- enantiomers of compound VII after application of the racemic mixture (3.0 mmol/kg).

The dependent claims relate to preferred embodiments.

It has emerged, surprisingly, that an additional substitution of the valproic acid framework or of a homolog thereof (with shorter or longer side chains on the carbon atom in position 2) in positions 5, 4, 3, 2, 2', 3' and/or 4' by a $C_1$–$C_6$-alkyl group is associated with a considerable reduction in the teratogenic effect.

This effect is particularly advantageous when the substituent, of which there is at least one and which branches the side chains bonded to the C-2 atom, is a methyl or ethyl group and, in particular, a methyl group. In this case, particularly preferred compounds have the formulae

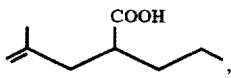  (V)

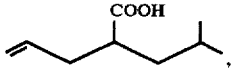  (VI)

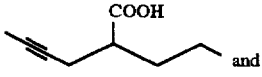  and (VII)

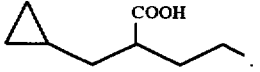  (VIII)

Besides the branching of the side chains it is therefore preferable in the compounds (I) and (II) for there also to be an unsaturated C—C bond, especially a double bond, at the carbon atom in position 4 and/or position 2'.

More particularly preferred compounds are V, VI and VII. Most particularly preferred is compound VII. As discussed below, compound VII has surprisingly been found to possess greater anticonvulsant activity compared to the other compounds tested. In addition, the pharmokinetics of compound VII demonstrates that its concentration in blood remains at active levels for a considerable longer duration than VPA. The combined increase of potency and decreased elimination will enables compound VII to be therapeutic at considerably lower doses, about 5 fold, than VPA. Another significant and unexpected advantage of compound VII is its lack of significant metabolism as shown in Example 11. Accordingly, it would be expected to have less potential for causing liver toxicity.

In the case where the carbon atom in position 2 is a center of asymmetry, the compounds have antiepileptic activity both in the form of their racemate and of their pure enantiomers or of a mixture of their enantiomers which differs from the racemate, and the teratogenicity in each of these cases is low. The teratogenicity is particularly low in the case of each of the R enantiomers.

Apart from the free carboxylic acids, it is also possible to employ their pharmaceutically compatible salts such as the alkali metal, alkaline earth metal or ammonium salts. The antiepileptic or anticonvulsant effect does not depend on whether the particular R or S enantiomer or a mixture of enantiomers is present, that is to say it does not depend on the stereochemistry in this respect (is not stereoselective).

Besides the reduced teratogenic effect, the sedative effect of the compounds according to the invention is also considerably reduced by comparison with that of valproic acid and, in some cases, was undetectable.

The compounds according to the invention are therefore excellently suited as antiepileptics.

The synthesis of achiral and racemic carboxylic acids is based on the generally known malonic ester synthesis, in that a dialkyl 2-alkylmalonate, for example the diethyl ester, with the formula

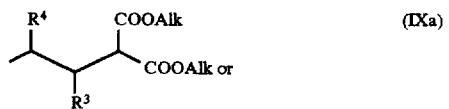  (IXa)

  (IXb)

Alk=methyl, ethyl is deprotonated with a base, such as, for example, sodium ethylate, and alkylated on the carbon in position 2 using an alkylating agent of the formula

  (X)

The dialkylated dialkyl malonate of the formula

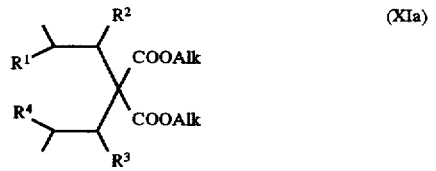  (XIa)

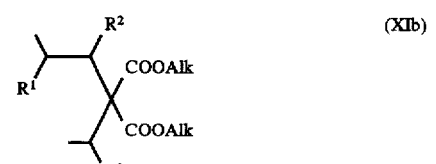  (XIb)

is subsequently subjected to alkaline hydrolysis, for example with potassium hydroxide in a water/ethanol mixture, and decarboxylated by heating in order to provide the required carboxylic acid. Depending on the unsaturation which is possibly present in the required product, the malonic ester employed as starting compound or the alkylating agent can also be unsaturated at the relevant positions.

Another embodiment of this invention is a method of treating individuals with epilepsy or those in need of anticonvulsant therapy with compounds of formulas I, II, III or IV. Mammals, and in particular humans, who would benefit from the method of treatment include those exhibiting, or at risk for exhibiting, any type of seizure. For example, methods are useful for treating individuals with ideopathic generalized seizures such as absence, myoclonic and tonic-clonic seizures and partial seizures. The method of the invention comprises administering to an individual a therapeutically effective amount of at least one compound of formulas I, II, III or IV which is sufficient to reduce or prevent seizure activity. Therapeutically effective amounts may be determined by titrating the amount of drug given to the individual to arrive at the desired effect while minimizing side effects Dosages may be similar to those used with VPA, however they may be adjusted accordingly based on the potencies and kinetic parameters disclosed herein. For example, compound VII would be expected to be useful at dosages which are about one fifth of those used for VPA. Preferably, doses for compound VII may be estimated to be between about 2 and 10 mg/kg body weight/day.

This invention also provides pharmaceutical compositions useful for providing anticonvulsant activity or comprising a compound of the invention. In addition to comprising at least one of the compounds described by formulas I, II, III or IV, the pharmaceutical composition may also comprise adjuvant substances and carriers. The compositions may be in the form of tablets, capsules, powders, granules, lozenges, suppositories, reconstitutable powders, or liquid preparations such as oral or sterile parenteral solutions or suspensions.

In order to obtain consistency or administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone, fillers, for example lactose, sugar, maize-starch, calcium phosphate, sorbitol or glycine; disintegrants, for example starch, polyvinylpyrrolidone, sodium starch glycolate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; nonaqueous vehicles (which may include edible oils), for example almond oil fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead or being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The dose of the compound used in the treatment of such disease will vary in the usual way with the seriousness of the disorders, the weight of the sufferer, and the relative efficacy of the compound.

General Method for the Synthesis:

3.1 g (135 mmol) of sodium are dissolved in 100 ml of absolute ethanol, and 25.6 ml (125 mmol) of diethyl 2-n-alkylmalonate in 50 ml of absolute ethanol are added. Subsequently, 150 mmol of freshly distilled alkyl halide (RX, see the exact names in the description of the individual compounds) are added dropwise in such a way that the reaction mixture just boils and refluxes until the reaction is complete (about 4 to 12 hours). Ethanol is removed under water pump vacuum; precipitated sodium halide is taken up in 150 ml of water, acidified with dilute HCl (pH <2) and extracted by shaking with diethyl ether (3×200 ml). The organic phase is dried over anhydrous sodium sulfate and stripped off under water pump vacuum. The remaining dialkylated malonic ester is purified by fractional distillation under high vacuum and added to a solution of 20.3 g (350 mmol) of potassium hydroxide in 50 ml of water and 100 ml of ethanol. The reaction mixture is heated to boiling under reflux until hydrolysis is complete (12 hours). Ethanol is stripped off under water pump vacuum, and the aqueous residue is mixed with 200 ml of water and extracted by shaking with diethyl ether (3×300 ml). The organic phase is discarded, and the aqueous phase is acidified dropwise, while stirring, with concentratyed HCl (pH <2) and extracted by shaking with diethyl ether (3×300 ml). The organic phase is dried over sodium sulfate and concentrated under water pump vacuum. The crude dialkylated malonic acid is, without further purification, heated in an oil bath at 160° to 180° C. and, after the decarboxylation is complete (4 hours), distilled twice under high vacuum.

The chromatographic and mass spectroscopic investigations were carried out as follows:

a) Chromatography methods

Silica gel plates with fluorescence indicator supplied by Merck (silica gel 60 $F_{254}$, 0.2 mm layer thickness) were used for the thin-layer chromatography. Besides UV detection, substance spots were visualized by spraying the silica gel plates with 50% concentrated sulfuric acid and heating to about 150° C. The mobile phases were mixtures of n-hexane and ethyl acetate (v/v). The following mobile phase mixture was used in the investigation of the α-branched carboxylic acids: 75 ml of n-hexane+20 ml of ethyl acetate+5 ml of acetic acid. The preparative column chromatography was carried out on silica gel 60 (0.040–0.063 mm, 230–400 mesh ASTM) supplied by Merck using the flash technique (Still et al., J. Org. Chem. 43, 2923–2925 (1978)).

b) Mass spectroscopy (coupled GC/MS)

The mass spectra of the TMS-carboxylic acids were obtained with the aid of a coupled GC-MS supplied by Hewlett Packard: (a) The GC, type HP 5890 A, was equipped with an HP-1 capillary column (12 mm long×0.2 mm internal diameter×0.33 pm film thickness). Helium was used as carrier gas, and the volume of gas flowing was 0.5 ml/min. The injector temperature was 250° C., and the initial column temperature, which was kept constant for 1 minute, was 70° C. The temperature was raised continuously to 170° C. at 10° C./min and kept constant for 1 minute. (b) The mass spectrometer, type 5971 MSD, was operated in scan-sensitivity electron impact ionization mode between masses (m/z) 60 and 270. The ionization energy was 70 eV. The temperature of the ion source was 180° C. and the GC interface was kept at 280° C. The MSD data system, Hewlett Packard G 1030 A Chem Station, was used to record the spectra. The relative percentage intensities of ions were based on the trimethylsilyl anion (m/z=73). The carboxylic acids were dissolved in methylene chloride and converted into the TMS esters of the carboxylic acids by adding MSTFA (room temperature, 2 h).

EXAMPLE 1

R,S-4-Methyl-2-n-propyl-4-pentenoic acid (V)

The synthesis is carried out by the general method indicated above, employing diethyl 2-n-propyl-malonate and 3-chloro-2-methylpropene as starting compound and alkylating agent respectively. The compound is purified by column chromatography on silica gel 60 (eluent: n-hexane/ethyl acetate/acetic acid=94/3/3).

Yield: 8.0 g (41%); Boiling point: 70° to 71° C./0.1 mbar; TLC: $R_f$=0.57; $^1$H-NMR (270 MHz/CDCl$_3$): δ=0.88 (t, J=7 Hz, 3H, 3'H), 1.20–1.65 (n, 4H, 1'H, 2'H), 1.70 (m, 3H, 4-CH$_3$), 2.07–2.20, 2.28–2.40 (2m, 2H, 3-H$_a$H$_x$), 2.48–2.64 (m, 1H, 2-H), 4.72 (d, J=11 Hz, 2H 5-H), 11.48 (s, (broad), 1H, COOH]. $^{13}$C-NMR (270 MHz/CDCl$_3$): δ=13.87, 20.45, 22.16, 34.08, 40.34, 43.57, 44.53, 112.23, 142.64, 182.63. GC-MS (TMS ester): retention time=5.96 minutes; m/z=213 (18%, M$^+$—CH$_3$), 199 (4%, M$^+$—C$_2$H$_5$), 186 (11%, X$^+$=C$_3$H$_4$).

EXAMPLE 2

R,S-2-n-Propyl-4-hexynoic acid (VII)

The synthesis is carried out by the general synthetic method indicated above, employing diethyl 2-n-propylmalonate and 1-bromo-2-butyne as starting compound and alkylating agent respectively. 1-Bromo-2-butyne was synthesized by the method described by K. E. Schulte and Reiss in Chemische Berichte 87, 964–970 (1954).

Yield: 6.9 g (36%); Boiling point: 94° C./0.2 mbar; TLC: $R_f$=0.46; $^1$H-NMR (270 MHz/CDCl$_3$): δ=0.93 (t, J=7.5 Hz, 3H, 3'-H), 1.28–1.47 (m, 2H, 2'-H), 1.54–1.73 (m, 2H, 1'-H), 1.76 (t, J=2 Hz, 3H, 6-H), 2.27–2.61 (m, 3H, 2-H, 3-H), 11.45 [S, (broad), 1H, COOH]. $^{13}$C-NMR (270 MHz/ CDCl$_3$): δ=3.32, 13.80, 20.21, 21.18, 33.18, 44.68, 75.80, 76.53, 181.55. GC-MS (TMS ester): retention time=7.17 minutes; m/z=211 (60%, M$^+$—CH$_3$), 184 (24%, M$^+$—C$_3$H$_6$), 183 (122%, M$^+$—C$_3$H$_7$).

EXAMPLE 3

R,S-2-(Cyclopropylmethyl)pentanoic acid (VIII)

The synthesis is carried out by the general synthetic method indicated above, employing diethyl 2-n-propylmalonate and chloromethylcyclopropane as starting compound and alkylating agent respectively.

Yield: 9.4 g (48%); Boiling point: 91°–93° C./1.2 mbar; TLC: $R_f$=0.58 $^1$H-NMR (270 MHz/CDCl$_3$): δ=−0.08–0.12 (m, 2H, C$_3$H$_5$—H$_{trans}$), 0.28–0.48 (m, 2H, C$_3$H$_5$—H$_{cis}$), 0.61–0.76 (m, 1H, C$_3$H$_5$—H$_x$), 0.89 (t, J=8 Hz, 3H, 5-H), 1.21–1.68 (m, 6H, 3-H, 4-H, C$_3$H$_5$CH$_2$), 2.46 (mc, 1H, 2-H), 12.04 [s (broad), 1H, COOH]. H$_a$ designates the proton on the tertiary carbon in the cyclopropane ring. The other ring protons are arranged cis or trans with respect to H$_a$ (H$_{cis}$ and H$_{trans}$ respectively). $^{13}$C-NMR (170 MHZ/CDCl$_3$): δ=4.31, 4.49, 8.99, 13.93, 20.53, 34.17, 37.24, 45.90, 183.52. GC-MS (TMS ester): retention time=6.74 minutes; m/z=213 (30%, M$^+$—CH$_3$), 199 (89%, M$^+$—C$_2$H$_5$), 186 (13%, M$^+$—C$_3$H$_6$).

EXAMPLE 4 (COMPARATIVE EXAMPLE)

R,S-2-n-Propyl-4-ipentynoic acid (XIII

The synthesis is carried out by the general synthetic method indicated above, employing diethyl 2-n-propylmalonate and propargyl chloride as starting compound and alkylating agent respectively.

Yield: 7.7 g (44%); Boiling point: 75°–76° C./0.7 mbar; Lit.: 82°–83° C./2 Torr [Cerbai et al. Farmaco, Ed. Sci. 27, 217–234 (1971)]. TLC: $R_f$=0.40; $^1$H-NMR (270 MHz/ CDCl$_3$): δ=0.94 (t, J=8 Hz, 3H, 3'-H), 1.28–1.50 (m, 2H, 2'-H), 1.57–1.81 (m, 2H, 1'-H), 2.02 (t, J=2.5 Hz, 5-H), 2.35–2.53 (m, 2H, 3-H), 2.54–2.70 (m, 1H, 2-H), 12.00 (s, 1H, COOH). $^{13}$C-NMR (270 MHz/CDCl$_3$): δ=13.71, 19.95, 20.65, 33.02, 44.05, 69.92, 81.06, 181.10. GC-MS (TMS ester): retention time: 5.31 minutes; m/z=197 (32%, M$^+$—CH$_3$), 170 (20%, M$^+$—C$_3$H$_6$), 169 (13%, M$^+$—C$_3$H$_7$).

EXAMPLE 5 (COMPARATIVE EXAMPLE)

R,S-2-n-Propyl-4-pentenoic acid (XIII)

The synthesis is carried out by the general synthetic method indicated above, employing diethyl 2-n-propylmalonate and allyl bromide as starting compound and alkylating agent respectively.

Yield: 8.7 g (48%); Boiling point: 87°–88° C./2.4 mbar; TLC: $R_f$=0.65; $^1$H-NMR (270 MHz/CDCl$_3$): δ=0.91, (t, J=8 Hz, 3H, 3'-H), 1.30–1.73 (m, 4H, 1'-H, 2'-H), 2.20–2.54 (m, 3H, 2-H, 3-H), 5.02–5.15 (m, 2H, 5-H), 5.80 (mc, 1H, 4-H), 12.05 (s, 1H, COOH). $^{13}$C-NMR (270 MHz/CDCl$_3$): δ=13.84, 20.36, 33.63, 36.07, 45.02, 116.84, 135.18, 182.51. GC-MS (TMS ester): retention time=5.01 minutes; m/z=199 (37%, M$^+$—CH$_3$), 185 (14%, M$^+$—C$_2$H$_5$), 172 (29%, M$^+$—C$_3$H$_4$).

EXAMPLE 6 (COMPARATIVE EXAMPLE

2-Methyl-2-propylpentanoic acid (XIV)

11.0 ml (70 mmol) of 2-n-propylpentanoic acid are added dropwise to 150 mmol of LDA solution (prepared from 21.0 ml of diisopropylamine in 100 ml of THF and 90 ml of n-BuLi (1.6M in n-hexane)). The reaction mixture is heated to 50° C. and stirred vigorously. After the metallation is complete, the mixture is cooled to room temperature, 4.4 ml (70 mmol) of methyl iodide are added, and the mixture is stirred for 2 hours. After acidification with 3 molar HCl (200 ml), the mixture is extracted by shaking with n-hexane (3×200 ml). The combined organic phases are dried over sodium sulfate and concentrated. The crystalline compound resulting after distillation under high vacuum is recrystallized from n-hexane.

Yield: 3.5 g (22%); Boiling point: 71° C./0.05 mbar; TLC: $R_f$=0.62; $^1$H-NMR (270 MHZ/CDCl$_3$): δ=0.91, (t, J=7 Hz, 6H, 5-H, 3'-H), 1.15 (s, 3H, 2-CH3) 1.19–1.44 and 1.56–1.68 (m, 8H, 3-H, 4-H, 1'-H, 2'-H), 12.12 (s, broad), 1H, COOH). $^{13}$C-NMR (270 MHZ/CDCl$_3$): δ=14.57, 17.76, 20.95, 41.48, 45.89, 184.94. GC-MS (TMS ester): retention time=9.07 minutes; m/z=215 (36%, M$^+$—CH$_3$), 188 (22%, M$^+$—C$_3$H$_6$).

The alkylation of the carboxylic acids at position 2 using alkyl halides is very generally possible with the aid of n-butyllithium at elevated temperature (Pfeffer et al., Alpha-anions of carboxylic acids. II. The formation and alkylation of alpha-metalated aliphatic acids. Journal of Organic Chemistry 37, 451–458 (1972). The methylation of the tertiary carbon atom of valproic acid is possible, for example, by deprotonation of the α-hydrogen atom at C-2 using n-butyllithium in hexane at 50° C. and subsequent methylation with methyl iodide at room temperature in a yield of 32%. The other 2-alkylated carboxylic acids can also be prepared in accordance with this method.

Synthesis of Enantiomeric Carboxylic Acids

It is possible to use chiral auxiliaries such as RAMP and SAMP or oxazolidinone auxiliaries for the synthesis of enantiomeric carboxylic acids.

The synthesis of the enantiomers of 2-n-propyl-4-hexynoic acid with the aid of chiral oxazolidinone auxiliaries is based on the asymmetric alkylation of chiral imide enolates which was described in 1982 by Evans et al. (J. Am. Chem. Soc. 104, 1737–1739 [lacuna] for example the commercially available oxazolidinones (XV) and (XVI)

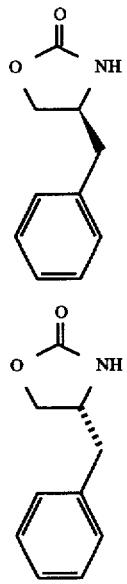

are used.

EXAMPLE 7

Synthesis of R-2-n-propyl-4-hexynoic acid
a) S-4-Benzyl-3-(1-oxopentyl)-2-oxazolidinone (XVII) The alkylating agent 1-bromo-2-butyne was prepared in analogy to the method described by Schulte and Reiss in Chem. Berichte 87, 964–979 (1954). 156.0 ml (255 mmol) of n-BuLi (1.6M in n-hexane) are added dropwise to 250 mmol of oxazolidinone in 330 ml of absolute THF at −78° C. (the orange-red of the dianion must just persist). After stirring for 1 hour, 30.7 ml (255 mmol) of freshly distilled valeroyl chloride are added dropwise. The reaction mixture is slowly warmed to room temperature and stirred for a further 4 hours. After the acylation is complete, the reaction is stopped by adding half-saturated ammonium chloride solution (200 ml). The volatile constituents are stripped off under water pump vacuum and the residue is extracted with methylene chloride (3×200 ml). The combined organic phases are washed initially with water and then with sodium chloride solution, dried over Na$_2$SO$_4$ and concentrated. The yellow crystalline N-acylated oxazolidinone crude product is purified by recrystallization in n-pentane.

[α]$_D^{22}$=53.2 (c=2.4, chloroform); Yield: 65.3 g (96%); $^1$H-NMR (270 MHz/CDCl$_3$): δ=0.95 (t, J=6.5 Hz, 3H, 5'-H), 1.42 (dt, J$_1$=8 Hz, J$_2$=6.5 Hz, 2H, 4'-H), 1.60–1.75 (m, 2H, 3'-H), 2.77 (dd, J$_1$=13.5 Hz, J$_2$=9 Hz, 1H, C$_4$H$_5$CH$_x$), 2.83–3.05 (m, 2H, 2'-H), 3.30 (dd, J$_1$=13.5 Hz, J$_2$=3 Hz, 1H, C$_4$H$_5$CH$_x$), 4.12–4.24 (m, 2H, 5-H), 4.63–4.73 (m, 1H, 4-H), 7.18–7.37 (m, 5H, C$_4$H$_5$).

b) (4S,2'R)-4-Benzyl-3-(1-oxo-2-n-propyl-4-hexynyl)-2-oxazolidinone

The alkylated oxazolidinone to be prepared is synthesized by adding 65 mmol of N-acylated oxazolidinone in 25 ml of absolute THF at −78° C. dropwise to 70 mmol of a freshly prepared LDA solution (prepared from 9.8 ml of diisopropylamine in 85 ml of absolute THF and 43.8 ml of n-BuLi (1.6M in n-hexane)). After stirring for 30 minutes, 80 mmol of 1-bromo-2-butyne are quickly added to the lithium enolate, and the reaction mixture is warmed to −20° C. in a very short time and then to 10° C. in the course of 6 hours. The reaction is stopped by adding half-saturated ammonium chloride solution (200 ml). The volatile constituents are stripped off under water pump vacuum, the residue is acidified (1 molar HCl) and extracted with methylene chloride (3×200 ml). The combined organic phases are washed first with water and then with saturated sodium chloride solution, dried over sodium sulfate and concentrated. The yellow oily alkylation product is purified by column chromatography (eluent: n-hexane/ethyl acetate=95/5).

Yield: 17.6 g (73%); [α]$_D^{24}$=+68.6 (c=2.2, chloroform) $^1$H-NMR (270 MHz/CDCl$_3$): δ=0.86–0.99 (m, 3H, 3"-H), 1.25–1.46 (m, 2H, 2"-H), 1.48–1.63 (m, 1H, 1"-H$_a$), 1.65–1.82 (m, 1H, 1"-H$_b$), 1.76 (t, J=3 Hz, 3H, 6'-H), 2.49 (mc, 2H, 3'-H), 2.77 (dd, J$_1$=13.5 Hz, J$_2$=9.5 Hz, 1H, C$_6$H$_5$CH$_x$), 3.29 (dd, J$_1$=13.5 Hz, J$_2$=3Hz, 1H, C$_6$H$_5$CH$_b$), 4.96 (dt, J$_1$=J$_2$=7 Hz, 1H, 2'-H), 4.12–4.25 (m, 2H, 5-H), 4.67–43.77 (m, 1H, 4-H), 7.19–7.38 (m, 5H, C$_6$H$_5$). The multiplet of the 1'-H is partly overlapped by the triplet of the 6' protons.

c) R-2-n-Propyl-4-hexynoic acid (R-VII)

To a solution, cooled to 5° C., of 30 mmol of alkylation product from b) in 400 ml of THF/water (3:1), initially 23.2 ml (136 mmol) of hydrogen peroxide (30% strength in water) and subsequently 2.5 g (60 mmol) of lithium hydroxide monohydrate in 65 ml of water are added dropwise. The reaction is complete after stirring for 6 hours and is stopped by adding a solution of 28.4 g (225 mmol) of sodium sulfite in 120 ml of water dropwise. THF is stripped off under water pump vacuum and the remaining aqueous phase is made alkaline (pH>10) with 5 molar sodium hydroxide solution. The oxazolidinone is extracted by shaking with methylene chloride (3×200 ml) and recovered from the organic phase. The aqueous phase is acidified (pH>2) with 1 molar HCl and

11 is extracted by shaking with diethyl ether (3×200 ml). The combined ether phases are dried over $Na_2SO_4$ and concentrated. The carboxylic acid is purified by distillation under high vacuum twice.

Yield: 4.1 g (88%); $[\alpha]_D^{25}=-2.2$ (c=2.3, chloroform); enantiomeric excess=96% The $^1$H-NMR (270 MHZ/CDCl$_3$) and $^{13}$C-NMR (270 MHz/CDCl$_3$) spectra are identical to those of the racemic compound VII.

EXAMPLE 8

S-2-n-Propyl-4-hexynoic acid (S-VII)

a) R-4-Benzyl-3-(1-oxopentyl)-2-oxazolidinone (XIX)

The method described above under Example 7 is used, starting from compound (XVI), to obtain R-4-benzyl-3-(1-oxopentyl)-2-oxazolidinone in a yield of 63.4 g (97%). $[\alpha]_D^{24}=52.5$ (c=2.0, chloroform).

b) (4R,2'S)-4-Benzyl-3-(1-oxo-2-n-propyl-4-hexynyl)-2-oxazolidinone (XX)

The synthesis is carried out as described in the previous examples.

Yield: 18.4 g (76%); $[\alpha]_D^{22}=67.2$ (c=2.0, chloroform)

C) S-2-n-Propyl-4-hexynoic acid (S-VII)

The synthesis is carried out as described in the previous example.

Yield: 4.0 g (87%); $[\alpha]_D^{23}=+2.1$ (c=2.2, chloroform); Enantiomeric excess=94%; The $^1$H-NMR (270 MHz/CDCl$_3$) and $^{13}$C-NMR (270 MHz/CDCl$_3$) spectra are identical to those of the racemic compound VII.

Reaction scheme

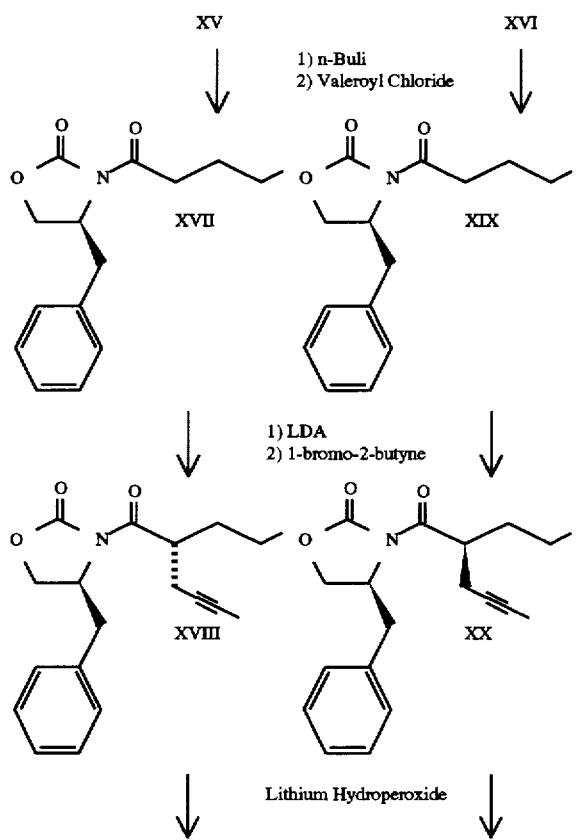

-continued
Reaction scheme

The enantiomers of the other compounds according to the invention can likewise be prepared by the method described above, it then merely being necessary to select the particular reagents corresponding to the required substitution pattern.

Of the enantiomers which are formed, in each case the R enantiomer is preferred because of its lower teratogenicity.

The following table shows that the compounds according to the invention are superior in respect of the antiepileptic effect, of the sedative effect and of the teratogenic effect or the exencephalic effect to the previously disclosed compounds considered as antiepileptic.

The anticonvulsant, sedative and teratogenic effects of the compounds according to the invention are determined by the methods described hereinafter.

The anticonvulsant effect of the carboxylic acids according to the invention toward subcutaneous administration of pentetrazole (PTZ) which has a convulsant action was determined by a modification of the subcutaneous pentetrazole convulsion test (PTZ test) described by Swinyard et al, Laboratory evaluation of antiepileptic drugs, Review of laboratory methods, Epilepsia 10, 107–119 (1969). Groups of 5 to 8 mice (NMRI or Swiss albino) are used for each substance and dose. The solutions of the sodium salts of the carboxylic acids are injected i.p. (1.50 mmol/kg) into the mice; 15 minutes later a solution of 65 mg of PTZ in 10 ml of physiological sodium chloride solution/kg body weight is administered subcutaneously into a skin fold on the back of the neck. The animals are subsequently observed for 30 minutes. The animals in which no clonic spasms persisting for at least 5 seconds occur in this period are regarded as protected within the scope of the PTZ test. PTZ alone induces clonic spasms which persist for more than 5 seconds, both in NMRI and in Swiss albino mice, after 6 to 12 minutes. These clonic spasms do not develop into tonic spasms.

The teratogenic effect of the carboxylic acids according to the invention was determined by the mouse exencephaly model described by Nau in Toxicol. Appl. Pharmacol. 80, 243–250 (1985) for investigating valproic acid and other compounds. Female NMRI mice are mated with male NMRI mice between 6.00 and 9.00 h. The first 24 hours after conception are regarded as day zero of gestation. The solution of the sodium salts of the carboxylic acids are injected i.p. into the mice between 7.00 and 9.00 h on day 8 of gestation. On day 18 of gestation, between 9.00 and 12.00 h, the animals are anesthetized with diethyl ether and subsequently the uterus is removed. The number of implantation sites and the resorptions and dead fetuses (embryolethality) is determined. Each live fetus is weighed and examined for exencephaly.

The sedative effect (maternal toxicity) of the carboxylic acids according to the invention was determined with the aid of the Rotorod toxicity test which was described by Dunham and Miya (The note on a simple apparatus for detecting neurological deficit in rats and mice, J. Am. Pharm. Assoc. 46, 208–209 (1957)). The solutions of the sodium salts of the carboxylic acids are injected i.p. in a dose of 1.50 mmol/kg into the mice. 15 minutes later the animals are tested to find whether they are still able to remain for 1 minute on the rod, rotating at 15 rpm, of the Rotorod apparatus (Rotorod, Ugobasile, Italy). This test is carried out on 5 to 7 mice for each substance. The mice must be able to stay on the rod of the Rotorod apparatus for at least 5 minutes before administration of the compounds.

TABLE 1

Teratogenicity of VPA and its analogs

| Substance | Dose (mmol/kg) | Live fetuses (n) | Fetal Weight (g) | Embryo lethality[a] (%) | Exencephaly[b] (%) |
|---|---|---|---|---|---|
| (I) $R^1$–$R^5$ = H | 3.00 | 122 | 1.07 ± 0.10 | 49 | 42 |
| (I) $R^1$ = $CH_3$, $R^2$–$R^5$ = H | 3.00 | 79 | 1.24 ± 0.07 | 3 | 1 |
| (VIII) | 3.00 | 108 | 1.13 ± 0.07 | 18 | 5 |
| (II) $R^3$ = $CH_3$, $R^1$, $R^2$, $R^4$, $R^5$ = H | 3.00 | 40 | 1.19 ± 0.10 | 18 | 0 |
| (II) $R^1$ = $CH_3$, $R^2$–$R^5$ = H | 3.00 | 46 | 1.23 ± 0.07 | 4 | 0 |
| (XII) | 2.47 | 13 | 0.86 ± 0.07 | 80 | 92 |
| (III) $R^4$—$CH_3$, $R^1$–$R^3$, $R^5$ = H | 3.00 | 69 | 1.19 ± 0.06 | 9 | 3 |
| (XIII) | 3.00 | 115 | 1.07 ± 0.10 | 17 | 35 |
| (V) | 3.00 | 128 | 1.15 ± 0.08 | 12 | 1 |
| (VI) | 3.00 | 86 | 1.20 ± 0.09 | 6 | 0 |
| Control NaCl | 3.00 | 126 | 1.14 ± 0.05 | 6 | 0 |

[a]Resorptions and dead fetuses as percentage of total implants
[b]Percentage of live fetuses with exencephaly

TABLE 2

Anticonvulsant and sedative effects of the compounds 15 minutes after i.p. administration of 1.5 mmol of Na salt/kg

| Substance | s.c. PTZ convulsion test[1] % | Rotorod toxicity test[2] % | ClogP |
|---|---|---|---|
| (I) $R^1$–$R^5$ = H | 100 | 33 | 2.720 |
| (I) $R^1$ = $CH_3$ $R^2$–$R^5$ = H | 100 | 67 | 3.119 |
| (VIII) | 100 | 20 | 2.635 |
| (II) $R^3$ = $CH_3$, $R^1$, $R^2$, $R^4$, $R^5$ = H | 80 | 67 | 2.590 |
| (II) $R^1$ = $CH_3$, $R^2$–$R^5$ = H | 100 | 33 | 2.590 |
| (XII) | 38 | 20 | 1.312 |
| (III) $R^4$ = $CH_3$, $R^1$–$R^3$, $R^5$ = H | 60 | 13 | 1.711 |
| (XIII) | 63 | 29 | 2.176 |
| (V) | 100a | 0 | 2.575 |
| (VI) | 100a | 0 | 2.575 | a100% at 1.25 mmol/kg
[1]Percent protection from convulsive episodes induced by s.c. pentylenetetrazol
[2]Percent of mice with minimal neurological deficits

TABLE 3

Average anticonvulsant dose, relative activity (compared with VPA) and gradient of the regression lines

| Substance | $ED_{50}$ (mmol/kg) | Relative activity | Gradient of the regression lines |
|---|---|---|---|
| (I) $R^1$–$R^5$ = H | 0.71 (0.48–1.08) | 1 | 1.66 (0.96–2.74) |

TABLE 3-continued

Average anticonvulsant dose, relative activity (compared with VPA) and gradient of the regression lines

| Substance | $ED_{50}$ (mmol/kg) | Relative activity | Gradient of the regression lines |
|---|---|---|---|
| (I) $R^1$ = $CH_3$ $R^2$–$R^5$ = H | 0.64 (0.41–1.11) | 1.11 | 1.46 (0.98–2.18) |
| (VIII) | 0.96 (0.64–1.14) | 0.74 | 1.61 (1.02–2.54) |
| (II) $R^3$ = $CH_3 R^1$, $R^2$, $R^4$, $R^5$ = H | 1.12 (1.03–1.19) | 0.63 | 1.29 (1.04–1.48) |
| (II) $R^1$ = $CH_3$, $R^2$–$R^5$ = H | 0.78 (0.52–1.16) | 0.91 | 1.38 (1.02–1.87) |
| (XII) | 1.78 (1.19–2.17) | 0.39 | 1.91 (1.02–3.59) |
| (XII) | 1.29 (1.00–1.57) | 0.54 | 1.48 (1.00–2.21) |
| (V) | 0.84 (0.56–1.28) | 0.85 | 1.45 (0.98–2.15) |
| (VI) | 1.01 (0.81–1.26) | 0.70 | 1.33 (1.10–1.61) |

Results calculated by the method of Litchfield and Wilcoxon, J. Pharmacol. Exp. Ther. 96, 99–113 (1949)
a95% confidence interval

TABLE 4

Comparison of the activities of compounds according to the invention with those of known compounds

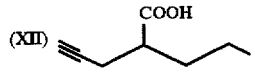

| | Anticonvulsant activity | Sedative activity | Teratogenic activity* |
|---|---|---|---|
| (XII) | 0.4 | 0.8 | (92%) |

TABLE 4-continued

Comparison of the activities of compounds according to the invention with those of known compounds

| | Anticonvulsant activity | Sedative activity | Teratogenic activity* |
|---|---|---|---|
| (XIII) CH₂=CH-CH₂-CH(COOH)-CH₂-CH₂-CH₃ | 0.5 | 0.9 | 35% |
| (V) CH₂=C(CH₃)-CH₂-CH(COOH)-CH₂-CH₂-CH₃ | 0.9 | 0.0 | 1% |
| (I) CH₃-CH₂-CH₂-CH(COOH)-CH₂-CH₂-CH₃ (R¹–R⁵=H) | 1.0 | 1.0 | 42% |
| (XIV) (H₃C)₂C(COOH)-CH₂-CH₂-CH₃ | 1.7 | 2.4% | 2% |
| (VII) H₃C-C≡C-CH(COOH)-CH₂-CH₂-CH₃ | 2.5 | 0.0 | 3% |

*Percent of live fetuses with exencephaly
**relative to valproic acid

Experimental Section

Chemicals: VPA and PTZ were obtained from Sigma (Deisenhofen, Germany). Methoxymethylbromide, propargylbromide, allylbromide, 2-butyn-1-ol, phosphorotribromide, cyclopropylmethylchloride, 3-chloro-2-methyl-I-propen, n-butylbromide, n-propylbromide, and benzylbromide were purchased from Aldrich (Steinheim, Germany).

Synthesis: The racemic mixtures of the compounds (1, 2, 4(XIII), 6, 7(XIV), 8, 10 (VIII), and 12(V); see structures) were synthesized by alkylation of diethyl-n-propylmalonate with the according alkyl-halides, subsequent alkaline hydrolysis, and decarboxylation according to the malonic ester synthetic procedures described above. Compound 2 was synthesized by hydratization of the C≡C triple bond of 3 (4-yn-VPA) with an acidified aqueous solution of mercury (II)-sulfate (Miocque, M., Nguye, Manh Hung; Vo, Quang Yen. *Ann. Chim.* 1963, 8, 157–174). Compound 7(XIV) was synthesized by a α-methylation of VPA after treatment with n-butyllithium (Pfeffer, P. E.; Silbert, L. S.; Chirinko, J. M., Jr. *J. Org. Chem.* 1972, 37, 451–458). Compound 5 was synthesized according to malonic ester synthetic procedures starting with the alkylation of diethylphenylmalonate with n-propylbromide.

Chemical purities of >99% were determined by gas chromatographic analysis of the TMS derivatives of the acids. Compound 9 was kindly provided by the Desitin Company (Germany).

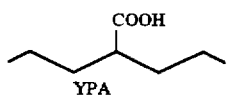

VPA

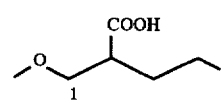

1

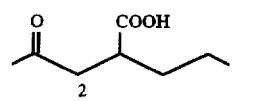

2

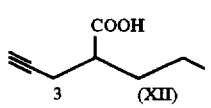

3 (XII)

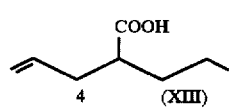

4 (XIII)

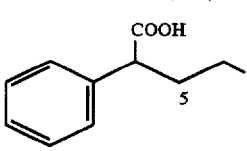

5

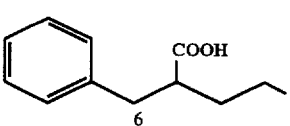

6

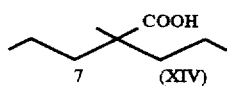

7 (XIV)

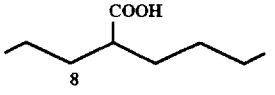

8

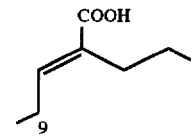

9

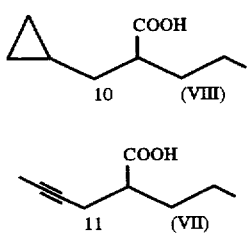

Lipophilicity was calculated according to Rekker and Mannhold (Calculation of Drug Lipophilicity; Rakker, R. F.; Mannhold, R., Eds.; VCH: Weinheim, New York, Basel, Cambridge, 1992; pp. 14–61).

Results

PTZ at 65 mg/kg (sc) was the minimal dose to produce threshold (clonic) seizures in 100% of the control animals. Higher doses (85 and 100 mg/kg), however, induced tonic extension of the hind limbs with some mortality.

Preliminary screening of the anticonvulsant activity of the tested compounds is shown in Table 5.

TABLE 5

Preliminary Screening of the Anticonvulsant and Neurotoxic Activities of All compounds*

| Substance | Chemical Formula | C log P | sc PTZ Seizure Threshold Test, % | Rotorod Toxicity Test, % |
|---|---|---|---|---|
| VPA (2-n-Propylpentanoic acid | $C_8H_{16}O_2$ | 2.720 | 100 | 33 |
| 1[(±)-2-(Methoxymethyl)pentanoic acid] | $C_7H_{14}O_3$ | 1.013 | 0 | 0 |
| 2[(±)-2-n-Propyl-4-oxo-pentanoic acid] | $C_8H_{14}O_3$ | 0.954 | 0 | 0 |
| 3[(±)-2-n-Propyl-4-pentynoic acid] | $C_8H_{12}O_2$ | 1.312 | 38 | 20 |
| 4[(±)-2-n-Propyl-4-pentenoic acid] | $C_8H_{14}O_2$ | 2.176 | 63 | 29 |
| 5[(±)-2-Phenylpentanoic acid] | $C_{11}H_{14}O_2$ | 2.781 | 80 | 80 |
| 6[(±)-2-Benzylpentanoic acid] | $C_{12}H_{16}O_2$ | 3.080 | 80 | 80 |
| 7(2-Methyl-2-n-propypentanoic acid) | $C_9H_{18}O_2$ | 3.119 | 100 | 80 |
| 8[(±)-2-n-Propylhexanoic acid] | $C_9H_{16}O_2$ | 3.249 | 100 | 80 |
| 9[E-2-n-Propyl-2-penenoic acid | $C_8H_{14}O_2$ | 2.586 | 100 | 60 |
| 10[(±)-2-(Cyclopropylmethyl)pentanoic acid] | $C_9H_{16}O_2$ | 2.635 | 100 | 20 |
| 11[(±)-2-n-Propyl-4-hexynoic acid] | $C_8H_{14}O_2$ | 1.841 | 100 | 0 |
| 12[(±)-4-Methyl-2-n-propyl-4-pentenoic acid] | $C_9H_{19}O_2$ | 2.575 | 100 | 0 |

*Tested 15 min after ip administration of 1.5 mmol sodium salt/kg. Percentage of mice protected from sc PTZ induces threshold seizures in groups of 5–8 mice. Percentage of mice showing minimal neurological deficits on a rotating rod in groups of 5–7 animals.

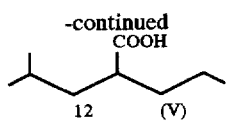

Animals: Male Swiss albino mice of an inbred strain, weighing 25–31 g, were maintained under controlled conditions of temperature (25° C.) and relative humidity (~50%) at the Islamic Centre for Medical Sciences in Kuwait.

Animal Experiments: A preliminary experiment was designed to compare the anticonvulsant and neurotoxic effects of all compounds with VPA. Anticonvulsant activity was measured by the sc PTZ seizure threshold test, and minimal neurotoxicity was evaluated by the rotorod toxicity test as described above.

In a follow-up experiment, compounds that showed a greater degree of anticonvulsant activity than of sedative activity were tested at various dose levels to calculate the median ($ED_{50}$) and maximal ($ED_{97}$) effective anticonvulsant doses and the relative potency as compared with VPA. In addition, compounds that showed maximum anticonvulsant protection with minimal neurotoxicity in the preliminary screening study were tested further at various dose levels on the rotorod to calculate minimal ($TD_3$) and median ($TD_{50}$) sedative doses.

Statistical Calculations: The values of $ED_{50}$, $ED_{97}$, $TD_3$, $TD_{50}$, slope of the regression line, potency, and slope ratios compared with VPA were calculated according to Litchfield and Wilcoxon. J. Pharm Exy. Ther., (1949) 96:99–113).

VPA (1.5 mmol/kg) produced 100% protection against PTZ-induced threshold seizures in mice. Similar anticonvulsant activity (100% protection) was shared by six other compounds (7–12) that produced the maximal anticonvulsant activity in equimolar doses (i.e., 1.5 mmol/kg). Two of these compounds (7 (XIV) and 11 (VII)) showed a similar effect (100% protection) when tried at a lower dose (1.0 mmol/kg). Four compounds (3–6) also produced significant anticonvulsant activity. Doses of 1.5 mmol/kg produced protection in 38–80% of the animals. Two compounds (1 and 2) showed no anticonvulsant activity at the dose used (1.5 mmol/kg).

The sedative activity of the compounds was assessed on the rotorod in the doses used for evaluation of anticonvulsant activity. The test was conducted at 15, 30, and 45 min after administration. The peak sedative effect was at 15 min. Compounds 1, 2, 11 (VII) and 12 (V) caused no sedation at a dose of 1.5 mmol/kg. Compounds 3 (XII), 4 (XIII), and 10 (VIII) produced sedation in 20–29% of the animals; this was slightly less than the sedation produced by VPA (33%). Compounds 5–9, however, produced higher sedation (60–80%) than did VPA (Table 5).

The compounds that showed a greater degree of anticonvulsant activity than neurotoxic activity in the preliminary screening test were tested further to evaluate their median effective dose ($ED_{50}$) and the relative potency compared with VPA (Table 6).

TABLE 6

Median Anticonvulsant Dose ($ED_{50}$) Relative Potency, and Slope of the Anticonvulsant Regression Line of the Compounds in Comparison with VPA*

| Substance | $ED_{50}$ mmol/kg | Relative Potency | Slope of Regression Line |
|---|---|---|---|
| VPA | 0.71 (0.48–1.08)$_b$ | 1.00 | 1.65 (0.96–2.74)$^c$ |
| 3(XII) | 1.78 (1.19–2.67) | 0.39$_c$ | 1.91 (1.02–3.59) |
| 4(XIII) | 1.29 (1.00–1.67) | 0.54$^c$ | 1.48 (1.00–2.21) |
| 7(XIV) | 0.40 (0.24–0.67) | 1.75 | 2.10 (1.18–3.74) |
| 8 | 0.78 (0.52–1.16) | 0.91 | 1.38 (0.84–2.26) |
| 9 | 0.68 (0.43–1.07) | 1.03 | 1.80 (1.28–1.94) |
| 10(VIII) | 0.96 (0.64–1.44) | 0.74 | 1.61 (1.02–2.54) |
| 11(VII) | 0.28 (0.16–0.50) | 2.54$^c$ | 2.58 (1.01–6.58) |
| 12 | 0.84 (0.56–1.28) | 0.85 | 1.45 (0.98–2.15) |

*Results are calculated and compared with those of VPA according to Litchfield and Wilcoxon, supra.
$^b$95% confidence interval.
$^c$p < 0.05.

The slopes of the anticonvulsant regression lines of the eight racemic acids tested was parallel, within experimental errors, to that of VPA. Compound 11 (VII) produced significantly higher potency than VPA (relative potency=2.5 times greater). Compounds 3 (XII) and 4 (XIII), however, showed lower potency. The other five compounds showed relative potencies of 0.73–1.75, which were not significantly different when compared with VPA.

Compounds 11 (VII) and 12 (V) (which showed no sedation at doses that produced maximum anticonvulsant protection) were found to have significantly less neurotoxicity that VPA when evaluated at various dose levels on the rotorod (Table 7).

TABLE 7

Anticonvulsant and Neurotoxic Profiles of 11 (VII) and 12 Compared with VPA

| Parameter | VPA | 11 | 12 |
|---|---|---|---|
| $TD_3$ | 1.20 | 2.0 | 2.15 |
| $TD_{50}^a$ | 1.65 (1.44–1.89)$^c$ | 2.3$^b$ (2.12–2.49) | 2.7$^b$ (2.41–3.02) |
| $ED_{50}^d$ | 0.71 (0.48–1.08) | 0.28$^b$ (0.16–0.50) | 0.84 (0.56–1.28) |
| $ED_{97}^d$ | 1.80 | 1.70 | 1.70 |
| PI$^e$ | 2.36 | 8.21 | 3.20 |
| Safety Ratio | 0.67 | 1.18 | 1.27 |

*$TD_3$ AND $TD_{50}$ are the minimal and median neurotoxic doses, respectively (mmol/kg)
$^b$p < 0.05.
$^c$95% confidence interval.
$^d$$ED_{50}$ and $ED_{97}$ are the median and maximal anticonvulsant doses, respectively (mmol/kg).
$^e$Protective Index = $TD_{50}/ED_{50}$.
$^f$Safety Ratio = $TD_3/ED_{97}$.

Both 11 (VII) and 12 (V) had higher protective indices and safety ratios than VPA. Compared with each other, 11 (VII) had higher protective index but with lower safety ratio than 12 (V) (Table 7). In addition, 11 (VII) had a longer duration of action when retested on the rotorod at 30 and 45 min after administration, infra.

Structure-Activity Relationships: One of the two 2-n-propyl groups of VPA was altered in all compounds (1–12), except 7 (XIV) and 9 (see structure). The α-hydrogen atom was substituted by a methyl group in 7 (XIV). In 9, the α-carbon atom is connected to only three groups because of the double bond, resulting in a planar structure ($sp^2$) instead of a tetrahedral one ($sp^2$)

Comparison of C log P (calculated lipophilicity) Calculation of Drug Lipophilicity: Rekker, R. F.; Mannhold, R., Eds., (1992) VCH: Weinheim, New York, Basel, Cambridge, 1992; pp.14–61 and anticonvulsant and neurotoxic activity (at a dose of 1.5 mmol/kg) of VPA and all compounds having only one alteration (1–12, except 7 and 9) is shown in FIG. 1. Compounds with low lipophilicity (1 and 2) were not centrally active. Compound 3 (XII) showed low activity. In contrast, 11 (VII), with an additional methyl group at the terminal triple bond of 3 (XII), resulted in a carboxylic acid containing nine carbon atoms ($C_9$) with high anticonvulsant activity and minimal neurotoxicity.

VPA is most widely employed clinically in absence and myoclonic seizures. Experimentally, it is characterized by a marked ability to increase PTZ seizure thresholds with relatively low effects (about half the potency) on seizure spread (antimaximal electroshock seizure) (Swinyard, E. A.; Woodhead, J. H. In *Antiepilentic Drugs*, 2nd ed.; Woodbury, D. M.; Penry, J. K.; Pippenger, C. E., Eds.; Raven: New York, 1982; pp. 111–126). Therefore, the PTZ-induced seizure threshold method was used to evaluate the anticonvulsant activity of the tested compounds and to calculate their relative potencies in comparison with VPA. The experiment was designed to identify compounds with anticonvulsant potencies equal to, or better than, that of VPA and with relatively less sedative effect. The test was carried out 15 min after i.p. administration of the compounds, a time that was found to show peak anticonvulsant effect.

VPA showed an $ED_{30}$ of 0.71 mmol/kg. Compounds 4 (XIII) and 9 have been evaluated previously (Löscher, W.; Nau, H. *Neuropharmacology* 1985, 24, 427–435) by the maximal electroshock seizure test and PTZ (100 mg/kg)-induced generalized tonic clonic seizures. The authors reported a lower potency for these two compounds and for VPA than found in the present experiment. The anticonvulsant activity of 3 (XII) was also investigated earlier (Hauck, R. S.; Elmazar, M. M. A.; Nau, H. *Naturwissenschaften* 1991, 78, 272–274). Compound 9 (2-en-VPA), the major active metabolite of VPA, showed anticonvulsant potency similar to that of VPA but a higher sedative action in the present study. Using other models, however, 2-en-VPA showed higher anticonvulsant and sedative potency than VPA (Loscher, W. Pharm. Weekbl./Sci./1992, 14(3A), 139–143).

Figure 2:
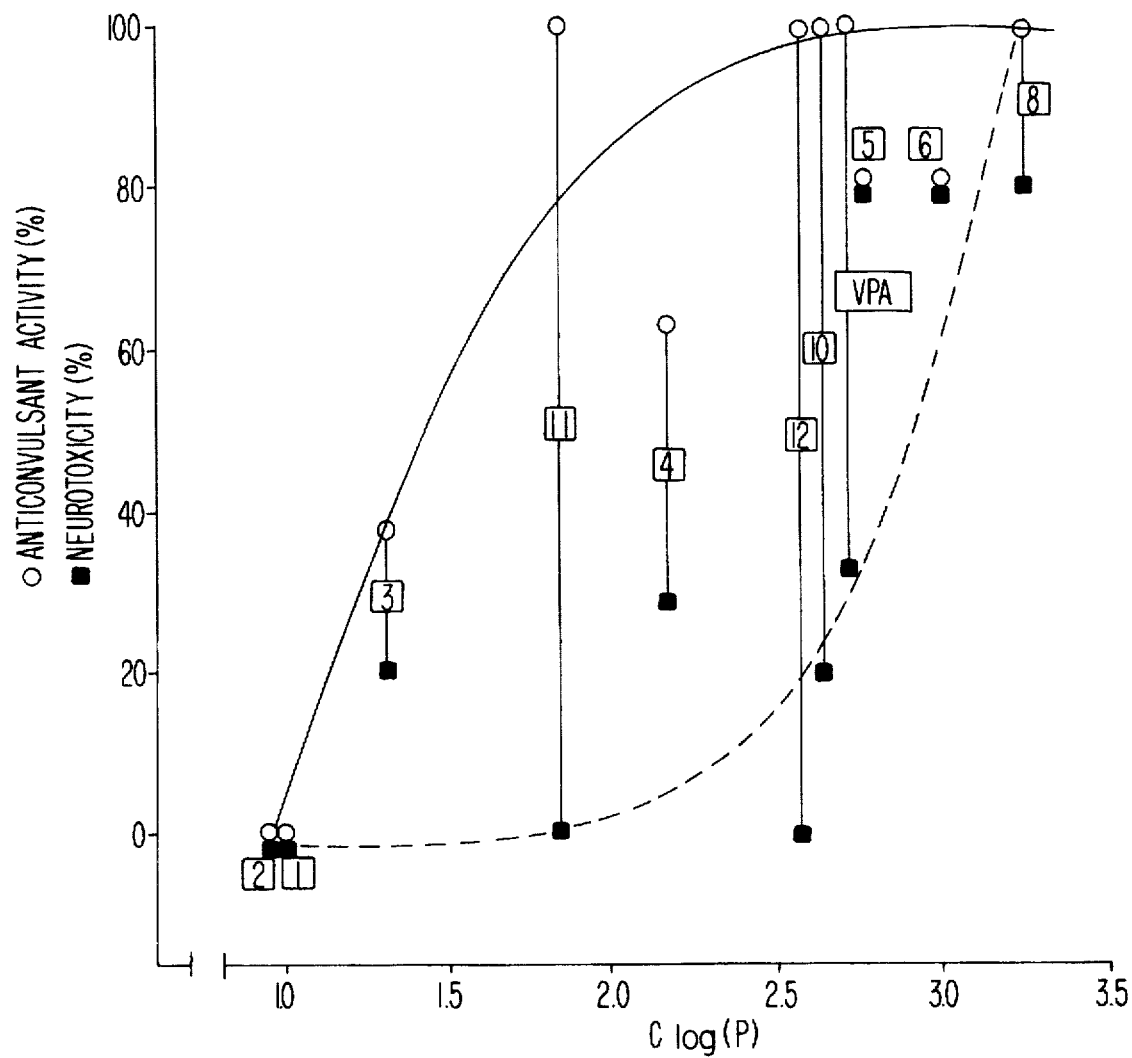
FIG. 2 Comparison of C log P (calculated lipophilicity) and anticonvulsant and neurotoxic activity (at a dose of 1.5 mmol/kg) of VPA and all compounds having only one alteration (1–12, except 7 (XIV) and 9). Compounds with low lipophilicity (1 and 2) were not centrally active. Compound 3 (XII) showed low activity. In contrast, 11 (VII) with an additional methyl group at the terminal triple bond of 3 (XII), resulted in a carboxylic acid containing nine carbon atoms ($C_9$) with high anticonvulsant activity and minimal neurotoxicity.
Figure 9A:
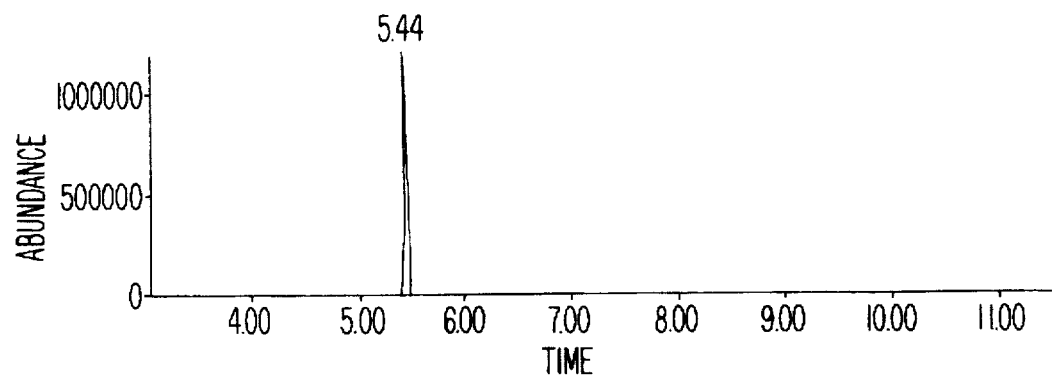
FIG. 9a. Reconstructed ion chromatogram of the M-15 ions of compound VII-TMS (m/z 211).
Figure 9B:
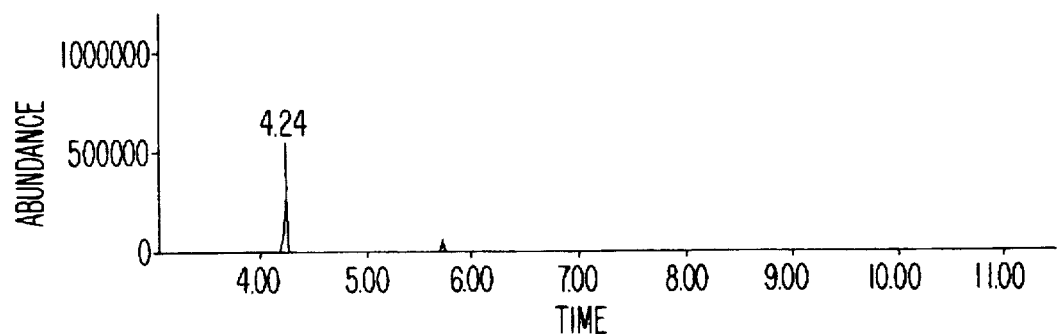
FIG. 9b. Reconstructed ion chromatogram of the M-15 ions of the internal standard (m/z 215).

Structure-Activity Relationships: The neurotoxic as well as anticonvulsant activity of a compound depends on molecular parameters, such as lipophilicity, which enable the compound to cross the blood-brain barrier and reach the cellular site of action. The neurotoxicity and anticonvulsant activity decreased in the order VPA (I)>4 (XIII)>3 (XII), see, Table 5 which was related to a similar decrease in lipophilicity of these substances (Hauck, R. S.; Elmazar, M. M. A.; Nau, H. Naturwissenschaften 1991, 78, 272–274). Thus, the influence of lipophilicity on neurotoxicity and anticonvulsant activity of VPA and structurally related carboxylic acids was investigated. Our results show (FIG. 9) that all acids with $C_9$ exhibit 100% anticonvulsant activity, whereas $C_8$ acids (other than VPA) produced lower anticonvulsant activity. Furthermore, the $C_9$ acids (10–12) showed minimal neurotoxicity. In general, with increasing lipophilicity (values about >2.6), the neurotoxicity increased to 80%. Therefore, for VPA-related compounds to produce central (anticonvulsant and sedative) actions, must possess a certain lipophilicity (about>1.0). Compounds with the desired high anticonvulsant activity and minimal neurotoxicity showed C log P values between 1.84 (11 (VII)) and 2.64 (10 (VIII)) and had nine carbon atoms. The $C_8$ acids with comparable lipophilicity (4) showed lower anticonvulsant and higher neurotoxicity (FIG. 2).

Compounds 11 (VII) and 12 (V) showed higher protective indices (TD$_{50}$/ED$_{50}$) and safety ratios (TD$_2$/ED$_{97}$) than that of VPA (Table 7), indicating that their maximum anticonvulsant protection is achieved in non-neurotoxic doses (Swinyard, E. A.; Woodhead, J. H. In *Antiepileptic Drugs*, 2nd ed.; Woodbury, D. M.; Penry, J. K.; Pippenger, C. E., Eds.; Raven: New York, 1982; pp. 111–126). Compound 11 (VII), on the other hand, showed longer duration of action than other compounds. This could be due to lower rates of metabolism and elimination (Hauck, R. S., et al., unpublished results). Lower metabolism and elimination rates were also observed for 3 (Hauck, R. S.; Elmazar, M. M. A.; Plum, C.; Nau, H. *Toxicol. Lett.* 1992, 60, 145–153). Both 3 (XII) and 11 (VII) contain a triple bond that may inhibit liver microsomal metabolizing enzymes (Oritz de Montellano, P. R.; Kunze, K. L. *Biochemistry* 1981, 20, 7266–7271) (Testa, B.; Jenner, P. Drug Metab. Rev. 1981, 12, 1–117) (Wilkinson, C. F.; Murray, M. Drug Metab. Rev. 1984, 15, 897–917) (Nau, H.; Hauck, R. S. Ehlers, K. *Pharmacol. Toxicol.* 1991, 69, 310–321).

Compared with VPA, both 11 (VII) and 12 (V) produced lower tetratogenicity and embryolethality in the mouse model (Nau, H.; Hauck, R. S. Ehlers, K., *Pharmacol. Toxicol.* 1991, 69, 310–321). Exencephaly rates of 3 and 1% for 11 (VII) and 12 (V), respectively, were induced by doses of 3.0 mmol/kg given i.p. at day 8 of gestation (compared with 44% exencephaly induced by the same dose of VPA).

Recently, it has been shown what the anticonvulsant activities of 4-yn-VPA (3 (XII) and 4-en-VPA (4 XIII) are independent of the stereochemical configuration of the respective enantiomers (Hauk et al., *Naturwissenchaften*, (1991) 78:272–274. Thus the anticonvulsant effect, in contrast to teratogenicity, may not be the consequence of stereoselective interaction with chiral biological structures.

EXAMPLE 10

Additional pharmacological data was obtained to further characterize compound VII in terms of anticonvulsant activity, sleep induction, and neurotoxicity using the assays described above.

TABLE 8

ANTICONVULSANT ACTIVITY

| SUBSTANCE | DOSE mmol/kg | ANIMALS PROTECTED (number of animals) | SLEEP INDUCTION AT 15 MIN. |
|---|---|---|---|
| VPA | 1.5 | 100% (8) | 20% |
|  | 1.0 | 60% (5) | 0% |
|  | 0.5 | 33% (6) | 0% |
| VII | 1.5 | 100% (5) | 0% |
|  | 1.0 | 100% (5) | 0% |
|  | 0.5 | 63% (8) | 0% |

TABLE 8-continued

ANTICONVULSANT ACTIVITY

| SUBSTANCE | DOSE mmol/kg | ANIMALS PROTECTED (number of animals) | SLEEP INDUCTION AT 15 MIN. |
|---|---|---|---|
|  | 0.25 | 50% (6) | 0% |
|  | 0.125 | 17% (6) | 0% |

Anticonvulsant activity is measured as percent protection against PTZ induced seizures. No sleep induction at 30 min. or 60 min.

TABLE 9

ROTOROD - TEST

| SUBSTANCE | DOSE mmol/kg | EFFECT 15 min | 30 min | 45 min |
|---|---|---|---|---|
| VPA | 2.4 (5) | 100% |  |  |
|  | 2.0 (5) | 80% | 40% | 20% |
|  | 1.5 (6) | 33% | 33% | 0% |
| VII | 2.5 (5) | 80% | 80% | 100% |
|  | 2.25 (5) | 40% | 80% | 80% |
|  | 2.0 (5) | 0% | 20% | 20% |
|  | 1.5 (5) | 0% | 0% | 0% |

TABLE 10

|  | VPA | VII |
|---|---|---|
| Percent protection in scPTZ Seizure Test | 100% | 100% |
| Percent failure in Rotorod Test | 33% | 0% |
| ED$_{50}$ mmol/kg (median anticonvulsant dose) | 0.71 (0.48–1.08) mmol/kg | 0.28 (0.16–0.50) mmol/kg (P < 0.05) |
| ED$_{97}$ (maximal anticonvulsant dose) | 1.8 mmol/kg | 1.7 mmol/kg |
| Relative potency (ED$_{50}$ VPA/ED$_{50}$ Compound) | 1.0 | 2.54 (P < 0.05) |
| TD$_3$ (minimal neurotoxic sedative dose) | 1.2 mmol/kg | 2.0 mmol/kg |
| TD$_{50}$ (median neurotoxic sedative dose) | 1.65 (1.44–1.89) mmol/kg | 2.3 (2.12–2.49) mmol/kg (P < 0.05) |
| PI (Protective Index; (TD$_{50}$/ED$_{50}$) | 2.36 | 8.21 |
| Safety Ratio (TD$_3$/ED$_{97}$) | 0.67 | 1.18 |

Compound VII showed a higher protective index and safety ratio than Valproate indicating that the maximum anticonvulsant protection is achieved in non-neurotoxic (sedative) doses.

Teratogenicity: Using the same assays described in Table I for determination of teratogenecity, compound VII was further compared with VPA.

TABLE 11

TERATOGENICITY TESTING

| DRUG | DOSE mmol/kg | NUMBER OF ANIMALS | LIVE FETUSES | FETAL WEIGHT (g) | EMBRYO LETHALITY | EXENCEPHALY |
|---|---|---|---|---|---|---|
| VPA | 3.0 | 8 | 60 | 1.07 ± 0.10 | 49% | 42% |
| VII | 2.0 | 3 | 35 | 1.06 ± 0.12 | 3% | 0% |
|  | 3.0 | 10 | 100 | 1.12 ± 0.10 | 7% | 3% |
| Control (Sodium Chloride) | 3.0 | 10 | 126 | 1.14 ± 0.05 | 6% | 0% |

Drug (sodium salt dissolved in water) administered to NMRI mice on day eight (8) of gestation, with analysis on gestation day 18. Embryo weight (mean (g) ±SD) embryolethality (% implantations) and exencephaly (% live fetuses) were measured.

EXAMPLE 11

Pharmacokinetics of Compound VII

The plasma kinetics of the compound VII enantiomers are described in Table 12 and FIG. 1. The racemic mixture of compound VII (3.0 mmol/kg of sodium salt i.p.) was administered to pregnant mice and blood samples were taken from the retero-orbital sinus under light anesthesia at different times post administration. The R and S enantiomers were analyzed in plasma using GC with nitrogen selective detection. The S-enantiomer is eliminated more slowly than the R-enantiomer. Because of the difference in plasma elimination between R- and S- VII, and rapid decline in the level of S- (at 14 h) after complete clearance of R- (data not shown); the effect of a high concentration of R- on the level of S- was studied. There was no difference at 5 h in the plasma levels of the S-enantiomer in the presence (504±35.3) and absence (536±28) of a high concentration of the R-enantiomers (2.5 mmol/kg, i.p., 1 h before and 4 h after s.c. injection of 2.5 mmol/kg S-enantiomer).

The pharmacokinetic parameters Cmax (µg/ml), t max (h), AUC (µg × h/ml) and Clearance (ml/kg xh) for the compound VII enantiomers, are described in Table 13 and compared to valproate. The half lives were not calculated due to insufficient time points; however, compound VII shows a significant longer duration of action than valproate. This may be due to lower rates of metabolism and elimination. Compound VII contains a triple bond that may inhibit the liver microsomal metabolism enzymes (Oritz de ontellano et.al. 1981, Testa & Lenner 1981, Wilkinson & Murray 1984).

Plasma, erythrocyte, embryonic and extra-embryonic levels of R- and S- VII and VPA were measured at 8 hours and 4 hours respectively after administration of 3.0 mmol/kg, of the racemic mixture of compound VII and VPA sodium salt, i.p. in day-9 pregnant NMRI mice. Blood samples were taken from the retero-orbital sinus under light ether anesthesia collected in heparinized tubes, centrifuged and plasma and erythrocytes were frozen until analyzed. Animals were killed by cervical dislocation and embryos and extraembryonic tissues (yolk sac) were dissected out, pooled and frozen until analyzed. The R- and S-enantiomers were analyzed using GC with nitrogen selective detection. The results are described in Table 14. Both enantiomers of compound VII demonstrate greater than 80% placental transfer. Extraembryonic tissues contain less drug.

TABLE 12

| | Plasma Levels (µg/ml) | | |
|---|---|---|---|
| TIME (h) | R-VII | S-VII | VPA |
| 0.25 | 430 ± 54 | 428 ± 50 | 718 ± 23.1 |
| 0.5 | 478 ± 53 | 483 ± 49 | 608 ± 15.0 |
| 1.0 | 497 ± 47 | 491 ± 44 | 544 ± 20.5 |
| 2.0 | 395 ± 18 | 420 ± 14 | 403 ± 77.7 |
| 4.0 | 317 ± 27 | 397 ± 32 | 82.1 ± 61.5 |
| 6.0 | 239 ± 61 | 356 ± 70 | 9.1 ± 5.3 |
| 8.0 | 141 ± 36 | 310 ± 70 | 4.5 ± 1.15 |
| 10.0 | 59 ± 7.4 | 215 ± 18.4 | |

Plasma kinetics of R- & S- VII after administration of (±) compound VII (3.0 mmol/Kg of the sodium salt, i.p., 0.1 ml/10 g) and VPA (3.0 mmol/kg) in day-8 pregnant NMRI mice. Blood samples were taken from the retero-orbital sinus under light ether anaesthesia at different times after administration. R- and S- VII were analyzed in the plasma using GC with nitrogen selective detection. The results from 5 animals are expressed as µg/ml ±SD

TABLE 13

| | Pharmacokinetic Parameters | | | |
|---|---|---|---|---|
| Enantiomer | Cmax (µg/ml) | $t_{max}$ (mins) | AUC (µg × h/ml) | CL/F$^c$ (ml/kg × h) |
| VPA | 718 ± 23.1 | 15 | 1616 | 267 |
| R-VII | 497 ± 47 | 60 | 2786 ± 362 | 83 ± 11 |
| S-VII | 491 ± 44 | 60 | 4027 ± 504 | 57 ± 7 |

The pharmacokinetic parameters were determined following administration of 3 mmol/kg of the racemic mixture of compound VII and 3 mmol/kg VPA. AUC=area under the concentration time curve.

TABLE 14

| | Levels R-VII | (µg/ml or g + SD) S-VII | (5 animals) VPA |
|---|---|---|---|
| Plasma | 87.3 ± 20.4 | 186 ± 26.1 | 195 ± 70 |
| Erythrocytes | 69.3 ± 19.4 | 150 ± 31 | |
| -Er/P | 79.4% | 80.7% | |
| Embryo | 71.1 ± 21.5 | 162 ± 32.4 | 202 ± 88 |
| -Em/P | 81% | 87% | 103.5% |
| Extra-embryonic | 35.4 ± 9.3 | 80 ± 12.8 | 145 ± 57 |
| | 40.5% | 43% | 74.4% |

METHOD OF SYNTHESIS: Compound VII was synthesized for use in this example as follows: 3.1 g (135 mmol) of sodium was dissolved in 100 ml of absolute ethanol, and 25.6 ml (125 mmol) of diethyl 2-n-propylmalonate in 50 ml of absolute ethanol was added. Subsequently, 150 mmol of freshly distilled 1-bromo-2-butyn are added dropwise in such a way that the reaction mixture just boils and refluxes until the reaction is complete (about 4 to 12 hours). Ethanol was removed under water pump vacuum; precipitated sodium halide was taken up in 150 ml of water, acidified with dilute HCl (pH<2) and extracted by shaking with diethyl ether (3×200 ml). The organic phase was dried over anhydrous sodium sulfate and stripped off under water pump vacuum. The remaining dialkylated malonic ester was purified by fractional distillation under high vacuum and added to a solution of 20.3 g (350 mmol) of potassium hydroxide in 50 ml of water and 100 ml of ethanol. The reaction mixture was heated to boiling under reflux until hydrolysis was complete (12 hours). Ethanol was stripped off under water pump vacuum, and the aqueous residue is mixed with 200 ml of water and extracted by shaking with diethyl ether (3×300 ml). The organic phase was discarded, and the aqueous phase was acidified dropwise, while stirring, with concentrated HCl (pH<2) and extracted by shaking with diethyl ether (3×300 ml). The organic phase was dried over sodium sulfate and concentrated under water pump vacuum. The crude dialkylated malonic acid was, without further purification, heated in an oil bath at 160° to 180_° C. and, after the decarboxylation was complete (4 hours), distilled twice under high vacuum.

Yield 6.9 g (36%)

The synthesis of R and S enantiomers of the compound is described in the Examples 7 and 8, together with the chromatographic and mass spectroscopy investigations.

REFERENCES:

Bjerkedal, T., Czeizel, A., Goujard, J., Kallen, B., Mastroiacova, P., Nevin, N., Oakley, G., Jr. and Robert E. (1982) Valproic acid and spina bifida. Lancet 2, 1096.

Binkerd, P. E., Rowland, J. M., Nau, H. and Hendrickx, A. G., (1988): Evaluation of Valproic Acid (VPA) Developmental Toxicity and Pharmacokinetics in Sprague-Dawley Rats. Fund. Appl. Toxicol.. 11, 485–493.

Carter, B. S. and Steward, J. M. (1989) Valproic acid prenatal exposure. Association with lipomyelomeningocele. Clin. Pediatr. 28, 81–85.

Davis, R.; Peters, D. H.; McTavish, D., (1994) Valproic acid. A reappraisal of its pharmacological properties and clinical efficacy in epilepsy. Drugs 47, 332–372.

Ehlers, K. H., Sturje, H. J., Merker and H. Nau, (1992) Valproic acid induced spina bifida: A mouse model Teratology 45, 145–154.

Elmazar, M. M. A., Hauck R.-S., and Nau H., (1993); Laboratory and Neurotoxic Activities of Twelve Analogues of Valproic Acid, Journal of Pharmaceutical Sciences 82, 1255–1258.

Hauck, R.-S. and Nau, H., (1991): On the Development of Alternative Antiepileptic Drugs: Lack of Enantioselectivity of the Anticonvulsant Activity, in Contrast to Teratogenicity, of 2-n-Propyl-4-pentenoic Acid and 2-n-Propyl-4-pentynoic Acid, Analogues of the Anticonvulsant Drug. Valproic Acid, Naturwissenschaften, 78, 272–274.

Hendrickx, A.G., Nau, H., Binkerd, P., Rowland, J. M., Rowland, J. R., Cukierski, M. J. and Cukierski, M. A., (1988): Valproic Acid Developmental Toxicity and Pharmacokinetics in the Rhesus Monkey: An Interspecies Comparison: Teratology, 38, 329–345.

Jager-Roman, E., Deichl, A., Jakob, S., Hartmann, A., Koch, S., Rating, D., Nau, H. and Helge, H. (1986) Fetal growth, major malformations and minor anomalies in infants born to women receiving valproic acid. J. Pediatr. 108, 997–1004.

Kao, J., Brown, N. A., Schmid, B., Goulding, E. H. and Fabro, S., (1981) Teratogenicity of Valproic Acid: In vivo and In vitro Investigations., Teratogen. Carcin. Mut. 1, 367–382.

Keane, P. E.; Simiand, J.; Mendes E.; Santucci, V.; Morre, M., (1983) Neuropharmacology 22, 875–879.

Litchfield, J. T., Jr.; Wilcoxon, F. J., (1949) Pharm. Exp. Ther. 96, 99–113.

Loscher, W.; Nau, H., (1985) Pharmacological Evaluation of Various Metabolites and Analogues of Valproic Acid. Anticonvulsant and Toxic Potencies in mice. Neuropharmacology 24, 427–435.

Mast, T. J., Cukierski, M. A., Nau, H. and Hendrickx, A. G., 1986: Predicting the Human Teratogenic Potential of the Anticonvulsant, Valproic Acid from a Non-Human Primate Model. Toxicology, 39, 111–119.

Nau, H., Hendrickx, A. G., (1987): Valproic Acid Teratogenesis, ISI Atlas Sci. Pharmacol 1, 52–54.

Nau, H., Loscher, W., (1986): Pharmacologic Evaluation of Various Metabolites and Analogs of Valproic Acid: Teratogenic Potencies in mice. Fundam. Appl. Toxicol. 6, 669–676.

Nau, H., Zierer, R., Spielmann, H., Neubert, D., and Gansau, C., (1981): A New Model for Embryotoxicity Testing: Teratogenicity and Pharmacokinetics of Valproic Acid following Constant-Rate Administration in the Mouse using Human Therapeutic Drug and Metabolite Concentrations; Life Sci. 29, 2803-2814.

Nau, H., (1985): Teratogenic Valproic Acid Concentrations: Infusion by Implanted Minipumps vs Conventional Injection Regimen in the Mouse. Toxicol. Appl. Pharmacol 80, 243–250.

Nau, H., Hauck, R.-S. and Ehlers, K., (1991): Valproic Acid-Induced Neural Tube Defects in Mouse and Human: Aspects of Chirality, Alternative Drug Development, Pharmacokinetics and Possible Mechanisms, Pharmacology & Toxicology 69, 310–321.

Ong, L. L., Schardein, J. L., Petrere, J. A., Sakowski, R., Jordan, H., Humphrey, R. R., Fitzgerald, J. E., and de la Iglesia, F. A., (1983): Teratogenesis of Calcium Valproate in Rats, Fundam. App. Toxicol 3, 121–126.

Petrere, J. A., Anderson, J. A., Sakowski, R., Fitzgerald, J. E., and de la Iglesia, F. A., (1986): Teratogenesis of Calcium Valproate in Rabbits. Teratology 34, 263–269.

Swinyard, et.al., (1969) Laboratory Evaluation of Antiepileptic Drugs, Review of Laboratory Methods, Epilepsia 10, 107–119.

Tein, I. and MacGregor, D. L. (1985) Possible valproate teratogenicity. Arch. Neurol. 42, 291–293.

Turner, S., Sucheston, M. E., de Philip, R. M., Paulson, R. B., (1990): Teratogenic Effects on the Neuroepithelium of the CD-1 Mouse Embryo Exposed in Utero to Sodium Valproate. Teratology 41, 421–442.

Vorhees, C. V., (1987): Teratogenicity and Development Toxicity of Valproic Acid in Rats, Teratology 35, 195–202.

EXAMPLE 11

Qualitative and quantative determination of compound VII and metabolites by gas chromatography/mass spectrometry in plasma, urine, liver and brain.

Single dose study: A single dose of 0.28 mmol compound VII/kg was administered i.p. and oral to the mice. Plasma, urine and tissue samples were taken 1 hour and 4 hours after treatment from groups of 3 animals per experiment. For the pharmacokinetic study, blood samples were taken over a time period up to 24 hours.

Extraction procedure: For all samples of plasma, urine and tissue homogenates the extraction procedure described by Nau et al.[1] and Fisher et al.[2] was used. To the samples (200 μl) 50 μl of phosphate buffer and 1 ml of ethyl acetate (containing an internal standard—I.S.—for quantitative measurements) were added. Samples were shaken for 15 min., centrifuged and the organic layers were transferred into glass reaction vials. Ethyl acetate was removed under a stream of nitrogen and the samples were derivatized by addition of 30 μl MSTFA (N-methyl-N-Trimethylsilyltrifluoracetamide). Aliquots of 1 μl were injected into the GC-MS systems.

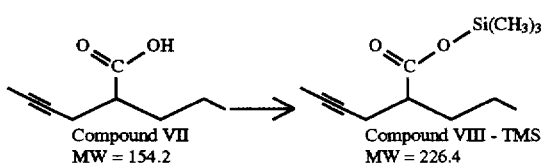

Compound VII
MW = 154.2

Compound VIII - TMS
MW = 226.4

GC-MS equipment: For quantitative determination we used a Perkin-Elmer F-22 gas chromatograph coupled to a Varian MAT CH-7A mass spectrometer controlled by the AMD Intectra DP 10 data system. The sample separation was carried out under temperature programmed condition (70°–210° C. with 20° C./min.) on a 60 m Restek Rtx-1701 Megabore column. The mass spectrometer was operated in the selected ion monitoring mode to measure substance specific ions (m/z 211 for compound VII and m/z 215 for I.S.).

A Hewlett Packard 5890 gas chromatograph coupled to a 59171A Mass Selective Detector was used to obtain the mass spectra of compound VII-TMS to show their presence in the samples and to look for possible metabolites. Sample separation was carried out under temperature programmed conditions (70°–220° C. with 10° C./min.) on a 25 m HP1701 special performance capillary column. The MSD was operated in electron impact ionisaiton (EI) mode and controlled by the HP DOS-ChemStation.

Figure 3:
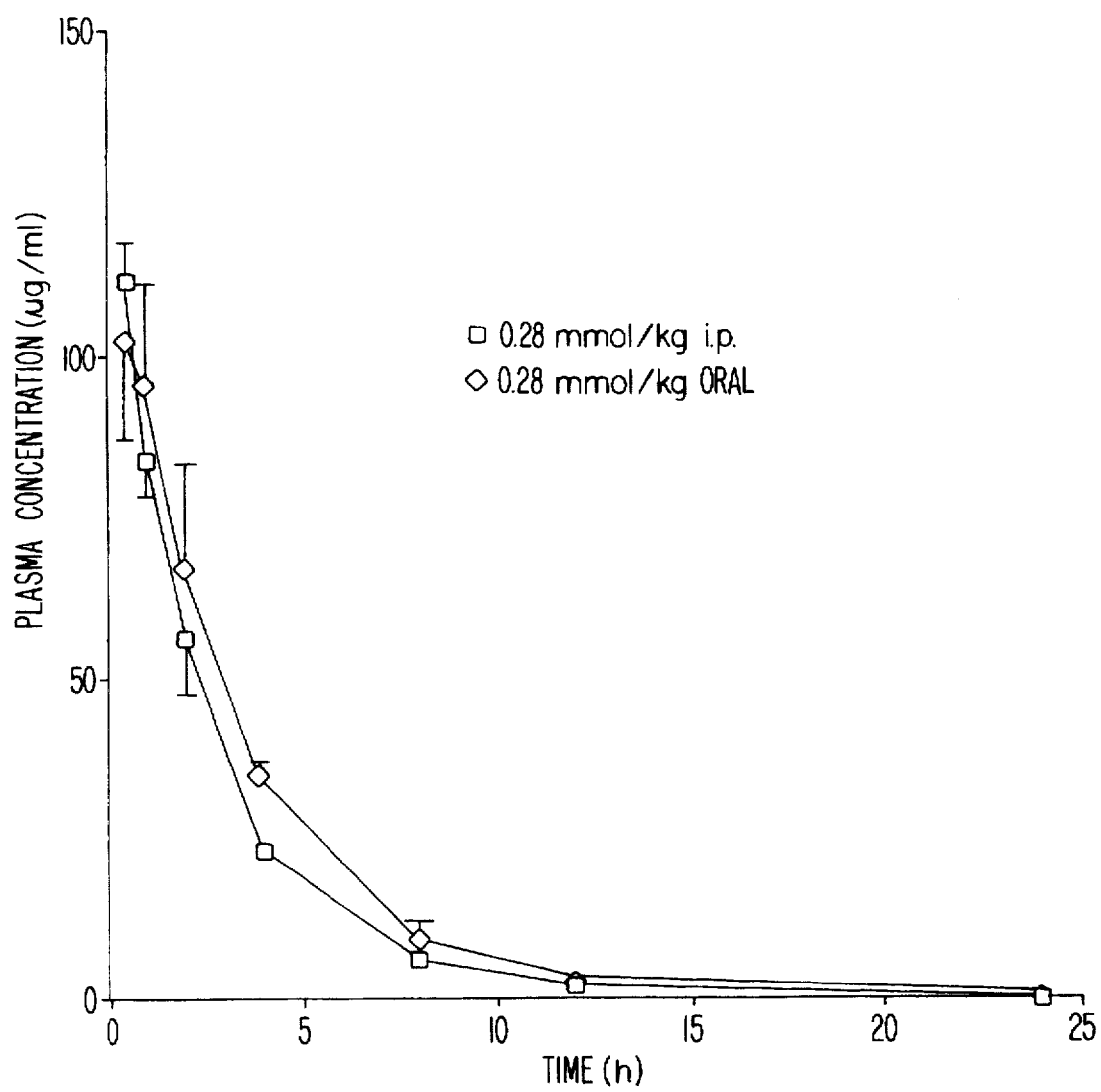
FIG. 3 Plasmas kinetics of oral and i.p. administered compound VII (0.28 mmol/kg).
Figure 4:
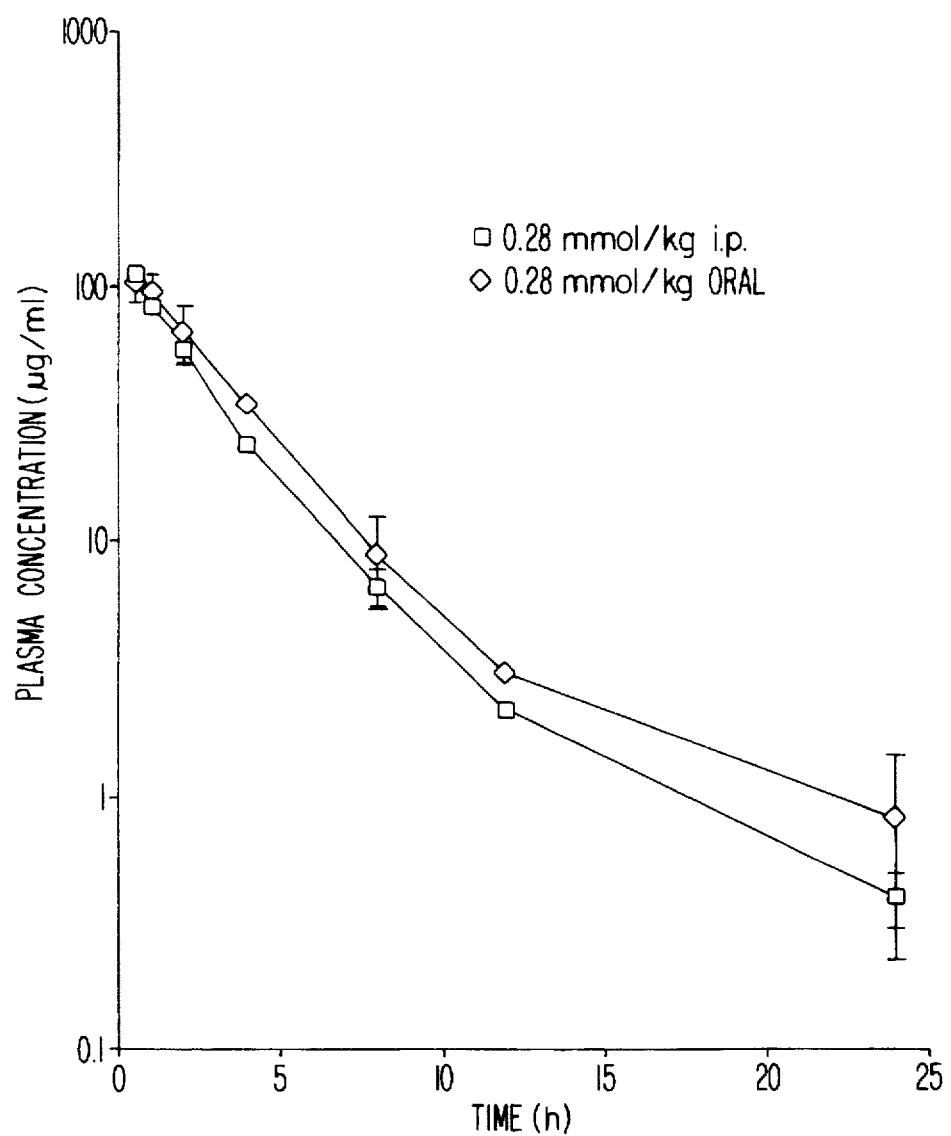
FIG. 4 Log transformation of plasma kinetic data from oral and i.p. administered compound VII (0.28 mmol/kg).

RESULTS:

Plasma Kinetics: Plasmas kinetics were performed following administration of 0.28 mmol/kg of compound VII (the ED-50 dose) via the oral and intraperitoneal routes in nonpregnant mice. The data are shown in Tables 15 and 16 and FIGS. 3 and 4. There is very little difference in the kinetics of either administration regimen. Both regimens resulted in very rapid absorption and maximal concentrations were already reached at the first time point examined. These data show that compound VII is readily bioavailable following oral administration. Table 16 describes the pharmacokinectic parameters obtained.

TABLE 15

Plasma Kinetics
Compound VII: Mouse Kinetics

| time/h | single dose: 0.28 mMol/kg i.p. *mean ± S.D. | oral *mean ± S.D. |
|---|---|---|
| 0.5 | 111.77 ± 5.96 | 102.04 ± 16.12 |
| 1 | 83.71 ± 5.47 | 94.81 ± 18.47 |
| 2 | 56.57 ± 7.59 | 66.73 ± 16.63 |
| 4 | 23.72 ± 0.50 | 34.10 ± 3.50 |
| 8 | 6.73 ± 1.21 | 8.87 ± 3.52 |
| 12 | 2.17 ± 0.10 | 3.06 |
| 24 | 0.41 ± 0.10 | 0.84 ± 0.61 |

*n = 3
Plasma kinetics of oral and i.p. administered ABS 103 (0.28 mmmol/kg).

TABLE 16

Pharmacokinetic Parameters

| P.k. Parameters | 0.28 mMol/kg i.p. | 0.28 mMol/kg oral |
|---|---|---|
| T ½ (h) | 2.1 h | 2.2 h |
| AUC μg h/ml | 322 | 390 |
| Cl ml/h kg | 143 | 121 |

Pharmacokinetic parameters obtained from plasma concentration curves following administration of 0.28 mmol/kg oral (n = 3) and i.p. (n = 3). The parameters were calculated using TOPFIT (a pharmacokinetic program).

Figure 5A:
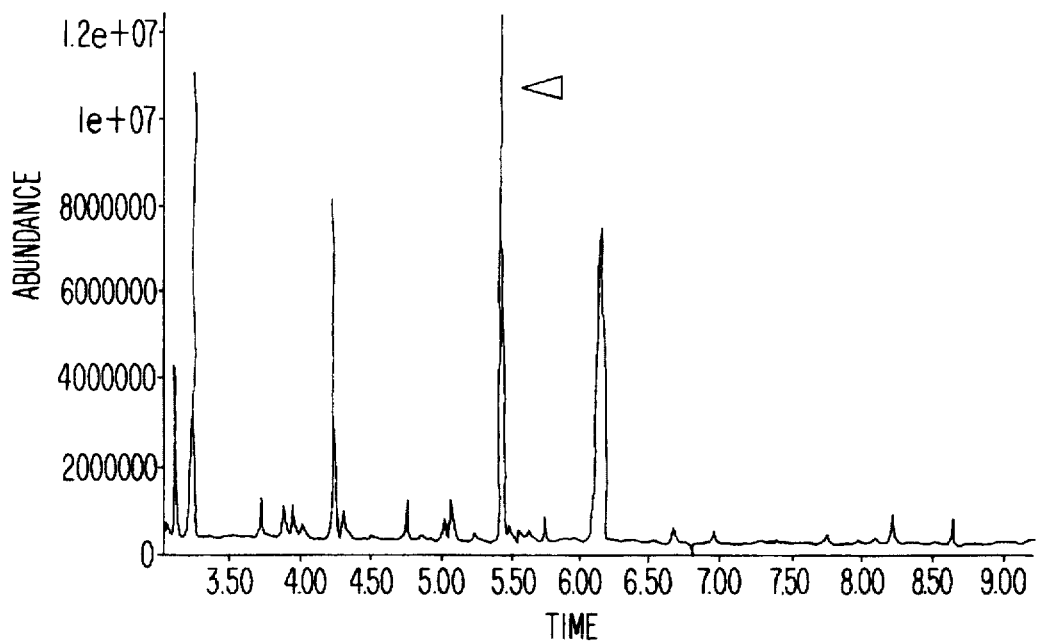
FIG. 5a: Total ion chromatogram of a mouse plasma sample. 4h post oral administration of 0.28 mmol/kg compound VII.
Figure 5B:
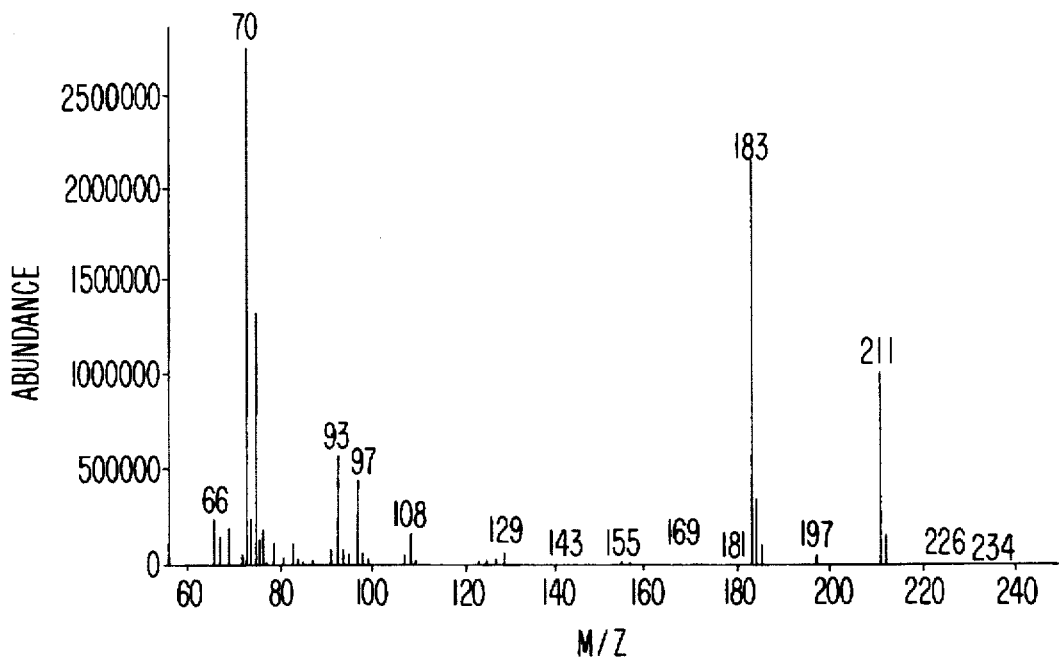
FIG. 5b: The mass spectrum of compound VII-TMS at a retention time of 5.436 min.
Figure 6A:
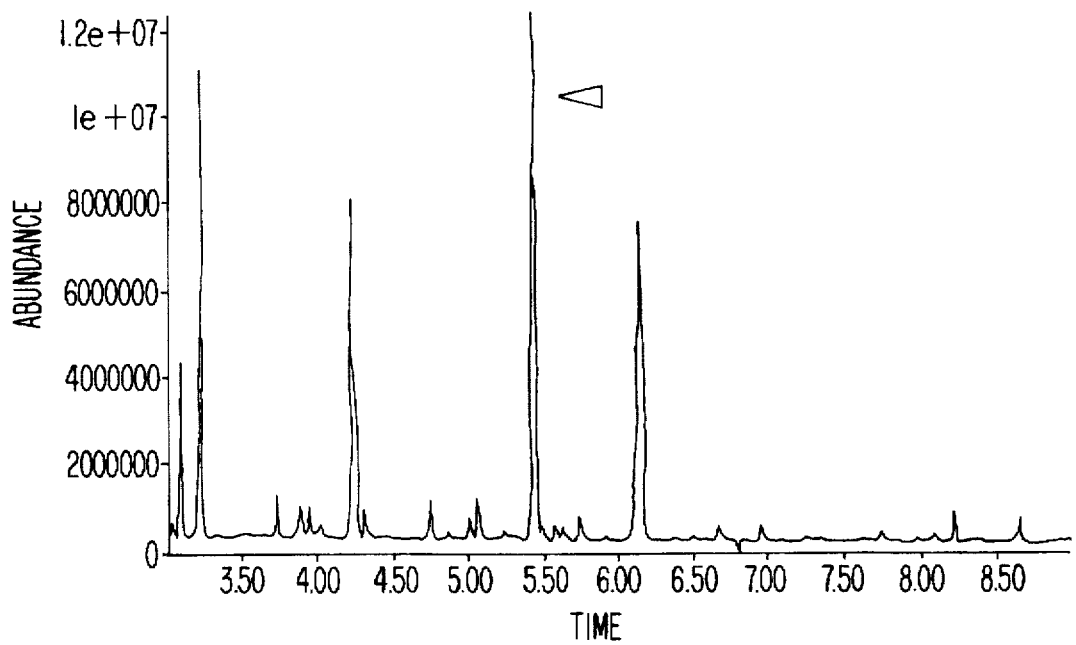
FIG. 6a: Total ion chromatogram of mouse plasma. 4 h post oral administration of 0.28 mmol/kg compound VII.
Figure 6B:
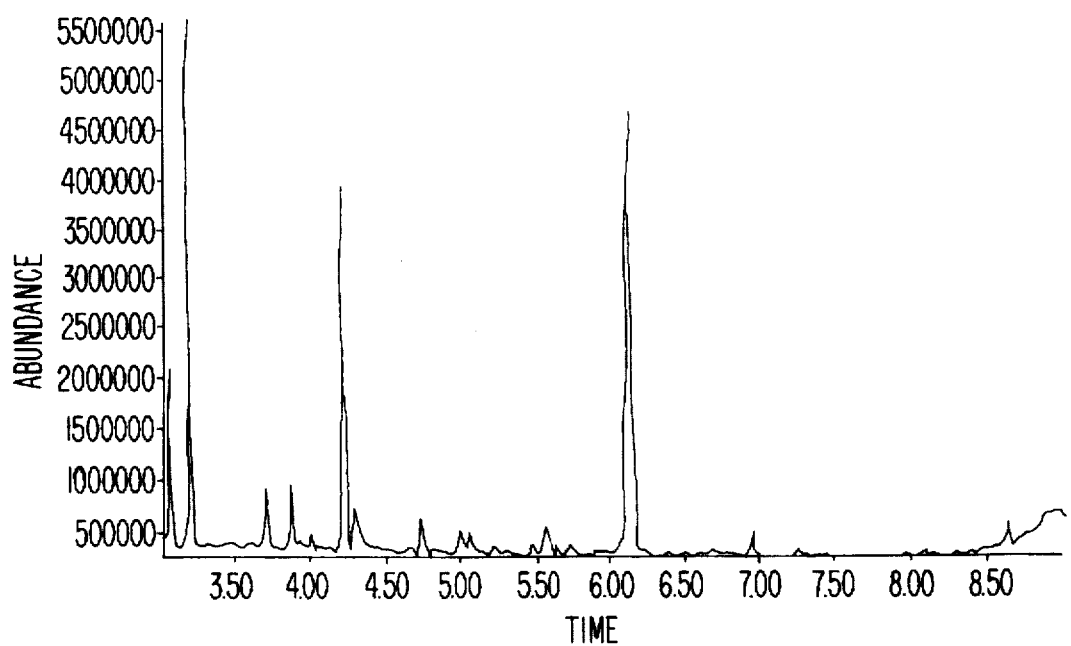
FIG. 6b: Ion chromatogram of control plasma.
Figure 7A:
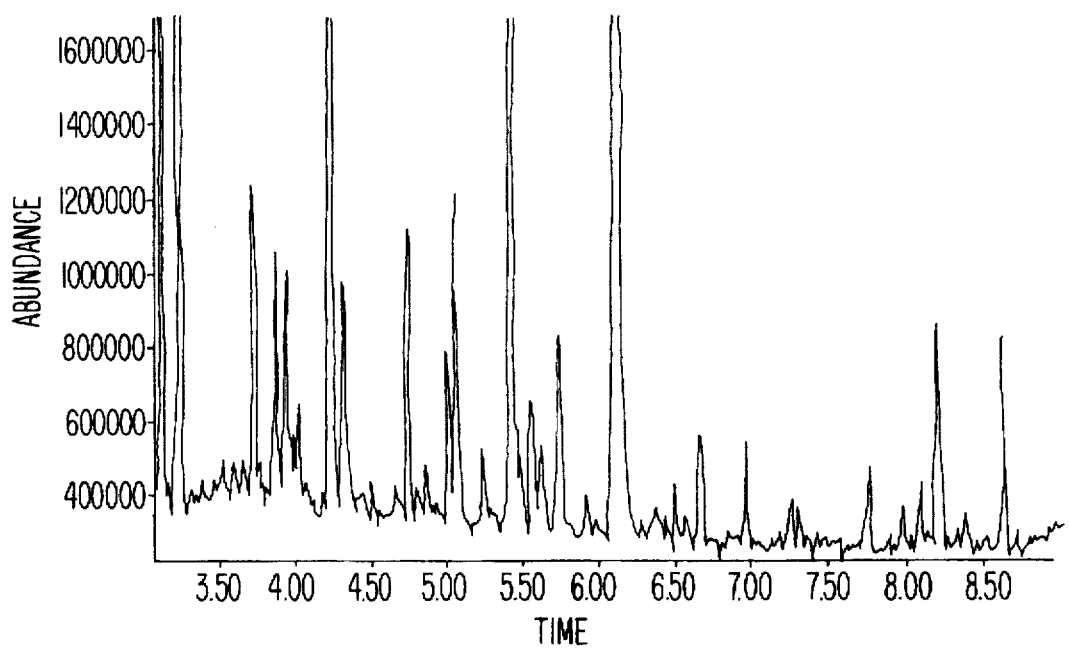
FIG. 7a. Same as FIG. 6a but with a higher magnification to compare the pattern of smaller peaks.
Figure 7B:
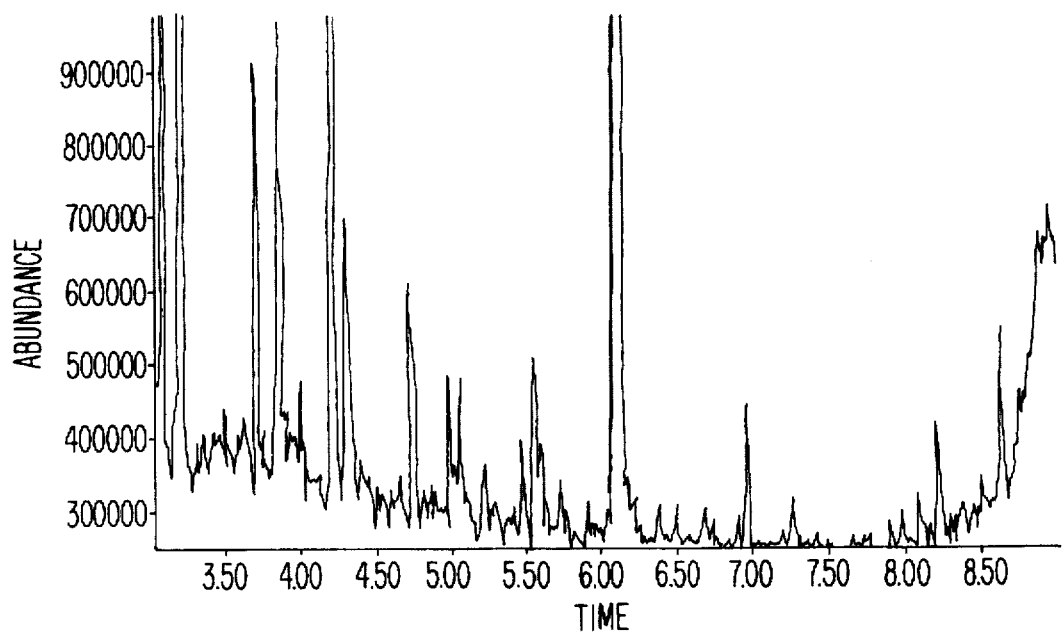
FIG. 7b. Same as FIG. 6b but with a higher magnification to compare the pattern of smaller peaks.
Figure 8A:
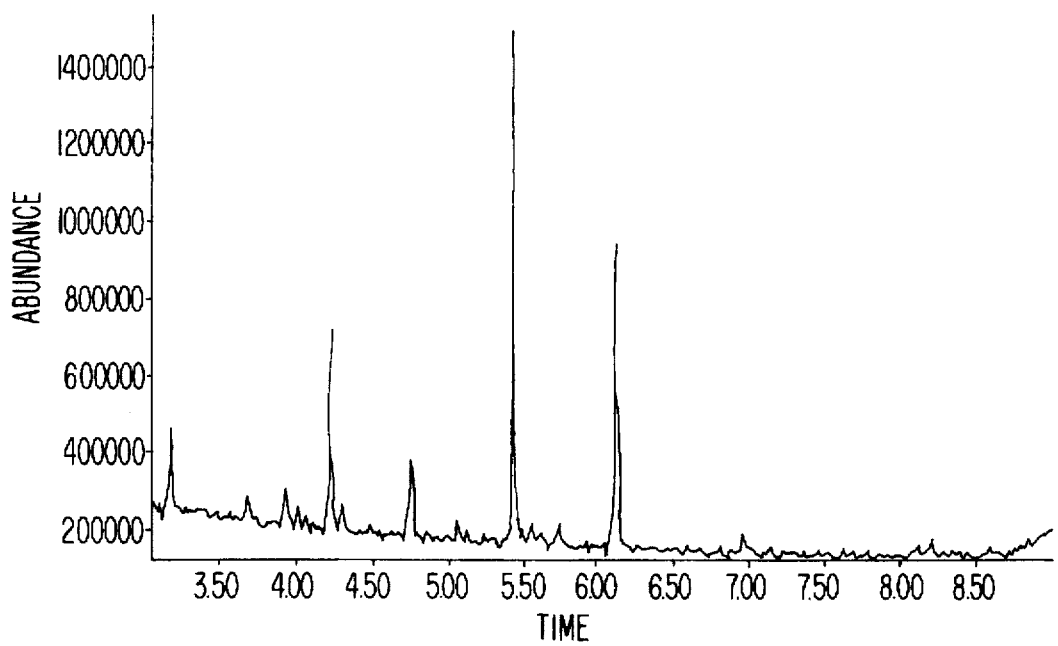
FIG. 8a. Ion chromatogram of plasma sample (i.p.) at 1 h post treatment.
Figure 8B:
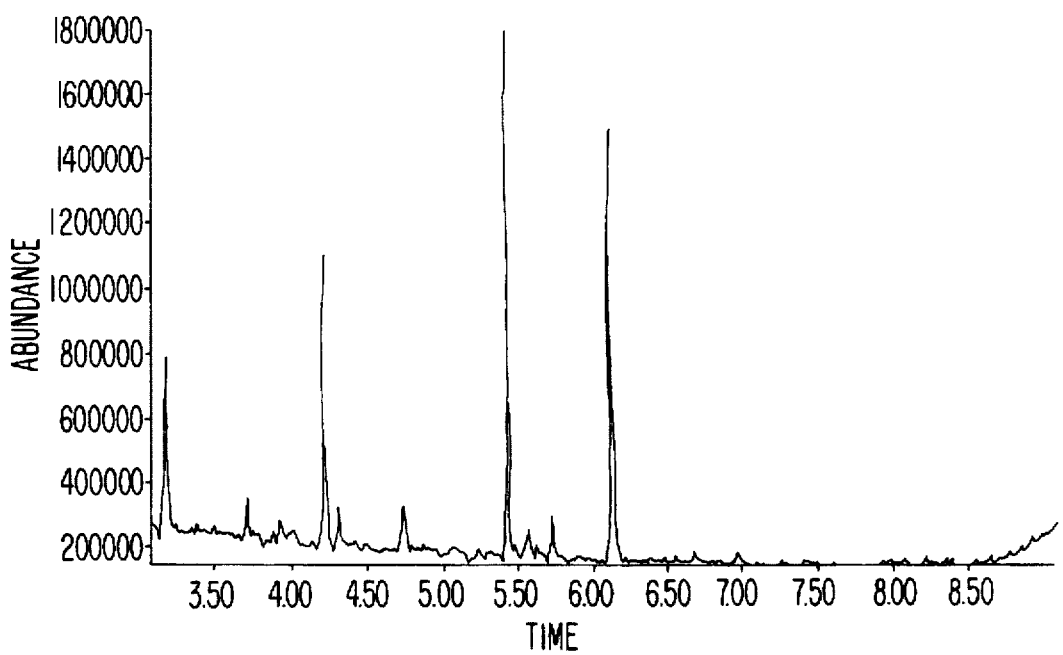
FIG. 8b. Ion chromatogram of plasma sample (i.p.) at 4 h post treatment.

Qualitative and metabolic study: In all samples we could find the exected compound VII TMS peak at the retention time of 5:436 min. FIG. 5 (top) shows the total ion chromatogram (TIC) with the compound VII-TMS peak and the well known internal standard peak. FIG. 5 (bottom) shows the mass spectrum of the compound VII-TMS. To see if there are additional peaks of interest, we compared plasma samples from treated vs. untreated mice. Surprisingly, additional peaks did not appear in any sample. FIG. 6 shows, that the only difference between the TICs of sample and control is the compound VII-TMS peak in the sample. FIG. 7 shows the same pattern in a higher magnification to compare the smaller peaks. The difference consist in only four small peaks and these peaks could be identified by their mass spectra as non-metabolic substances. The difference in the peak intensities can be explained by the fact that the samples are not from the same animal. In the same manner, we compared the one hour with the four hour samples and it can be seen in FIG. 8, that there is also no difference in the chromatograms. The selected ion monitoring recordings are shown for m/z 211 compound VII and for m/z 215 (the internal standard) used in FIG. 9.

The second possibility to search for metabolites is to assume that compound VII has a similar metabolic pathway to VPA, 2-en-VPA or 4-en-VPA. We therefore used the calculated ions for such suspected metabolites to reconstruct ion chromatograms such as those shown for compound VII and the I.S. in FIG. 7, but no metabolites could be detected.

Plasma transfer: The transfer of compound VII to brain and liver are shown in Table 17. In general, brain levels are about ⅒th of corresponding plasma levels, liver concentrations are about ½ of corresponding plasma levels.

The extent of conjugation of compound VII in urine was determined by treating urine with β-glucuronidase-aryl sulfatase to hydrolyse conjugates of the drugs/metabolites. Compound VII was conjugated considerably as expected, but additional peaks did not appear (Table 18). These studies indicate that conjugates of compound VII are present, probably the μ-glucuronide, but other metabolites are essentially not formed from compound VII in mice after a single dose administration. These studies suggest very low, if any, metabolism of compound VII with the exception of the formation of conjugates. Thus, plasma metabolites do not appear to complicate the pharmacokinetics of compound VII. The low metabolism of compound VII is also mirrored by the relatively slow elimination of compound VII as compared to valproate (previously described).

Plasma Protein Binding: Finally, plasma protein binding of compound VII was determined (Table 19). The percent free drug determined from oral and i.p. studies is 23.5±4.41%.

TABLE 17

Quantitative determination of Compound VII
Compound VII: concentrations in liver, brain and plasma

| sample | time | concentration in μg/ml | |
|---|---|---|---|
| | | i.p. | oral |
| liver | 1 h | 38.34 ± 5.71 | 53.98 ± 9.69 |
| | 4 h | 17.71 ± 3.51 | 9.87 ± 5.24 |
| brain | 1 h | 8.54 ± 3.79 | 7.54 ± 0.29 |
| | 4 h | 3.62 ± 1.15 | 3.22 ± 0.59 |
| plasma | 1 h | 92.45 ± 8.75 | 93.00 ± 6.20 |
| | 4 h | 27.38 ± 2.20 | 30.75 ± 0.49 |

The above results were obtained by using an internal standard added during the extraction procedure and GC-MS system operating in single ion mode. Concentrations were calculated from peak area ratios (Compound VII/I.S.).

TABLE 18

Hydrolysis of conjugated Compound VII
urine ± glucuronidase/arylsuphatase/urease

| treatment | time | concentration in μg/ml | | % |
|---|---|---|---|---|
| | | total* | non-conj. | non-conj. |
| oral | 1 h | 702.7 | 235.0 | 33.4 |
| oral | 4 h | 480.7 | 229.7 | 47.8 |
| i.p. | 1 h | 738.5 | 326.8 | 44.2 |
| i.p. | 4 h | 464.2 | 299.9 | 64.6 |

*conjugated + non-conjugated
Urine sampels were divided in two portions, one for direct extraction (unconjugated part) and the other for measuring the total concentration. The total concentration of Compound VII was determined by adding 50 μl of phosphate buffer pH 5.0, 20 μl β-glucuronidase-arysulphatase and 20 μl urease S (to remove the large amounts of urea) to the urine samples (<30 μl). Samples were slowly agitated at 37° C., extracted and measured.

TABLE 19

Ultrafiltration to determine free
Compound VII in plasma

| treatment | time | concentration in μg/ml | | % |
|---|---|---|---|---|
| | | total | non-conj. | non-conj. |
| oral | 1 h | 97.4 | 17.8 | 18.3 |
| | 1 h | 88.6 | 18.8 | 21.2 |
| oral | 4 h | 30.4 | 7.7 | 25.3 |
| | 4 h | 31.1 | 5.2 | 16.7 |
| i.p. | 1 h | 103.3 | 28.0 | 27.1 |
| | 1 h | 81.6 | 17.6 | 21.6 |
| i.p. | 4 h | 28.9 | 8.1 | 28.0 |
| | 4 h | 25.8 | 7.6 | 29.5 |

From each plasma sample, an aliquot of 100 μl was used to determine the total concentration of Compound VII and another 100 μl was used to measure the free concenttraion of Compound VII. To determine the concentration of non-conjugated Compound VII, we used the commercially available MPS-1 system with YMT membranes from Amicon, Danvers, MA, which is described as a micropartion system for separation of free from protein-bound substances. From the results presented in the above table, we obtained a free-drug fraction of 23.5 ± 4.4%.

REFERENCES:

Nau, H., et al., J. Chromatoa. 1981.

Fisher, E., Witfoht, W., Nau, H. (1992). The quantitative determination of valproic acid and 14 metabolites in serum and urine gas chromatography/mass spectrometry. J. Biomed Chromatog. 6, 24–29.

We claim:

1. A method of reducing seizure activity in an individual, comprising administering a therapeutically effective amount of 2-n-propyl-4-hexynoic acid or a pharmaceutically compatible salt thereof, wherein the form of the 2-n-propyl-4-hexynoic acid is chosen from the racemate, a single enantiomer, or a non-racemic mixture of enantiomers.

2. The method of claim 1, wherein the compound is (R)-2-n-propyl-4-hexynoic acid or a pharmaceutically compatible salt thereof.

3. The method of claim 1, wherein the compound is (S)-2-n-propyl-4-hexynoic acid or a pharmaceutically compatible salt thereof.

4. The method of claim 1, wherein the compound is a pharmaceutically compatible salt of 2-n-propyl-4-hexynoic acid.

5. The method of claim 2, wherein the compound is a pharmaceutically compatible salt of (R)-2-n-propyl-4-hexynoic acid.

6. The method of claim 3, wherein the compound is a pharmaceutically compatible salt of (S)-2-n-propyl-4-hexynoic acid.

* * * * *